United States Patent
Janiyani et al.

(10) Patent No.: US 7,807,410 B2
(45) Date of Patent: Oct. 5, 2010

(54) **REGULATORY ELEMENTS OF COLD-INDUCIBLE *HUTU* GENE FROM THE ANTARCTIC PSYCHROTROPHIC BACTERIUM *PSEUDOMONAS SYRINGAE***

(75) Inventors: Kamala L. Janiyani, Hyderabad (IN); Malay Kumar Ray, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 368 days.

(21) Appl. No.: 11/797,895

(22) Filed: May 8, 2007

(65) Prior Publication Data

US 2008/0268523 A1 Oct. 30, 2008

Related U.S. Application Data

(63) Continuation of application No. 10/349,308, filed on Jan. 23, 2003, now abandoned.

(60) Provisional application No. 60/351,529, filed on Jan. 25, 2002.

(51) Int. Cl.
*C12P 21/02* (2006.01)

(52) U.S. Cl. ..................... 435/69.1; 435/91.41; 435/6

(58) Field of Classification Search ..................... None
See application file for complete search history.

(56) References Cited

U.S. PATENT DOCUMENTS

| | | |
|---|---|---|
| 4,824,782 A | 4/1989 | Furutani et al. |
| 5,728,519 A | 3/1998 | Levenbook et al. |
| 5,942,496 A | 8/1999 | Bonadio et al. |
| 5,994,076 A | 11/1999 | Chenchik et al. |

OTHER PUBLICATIONS

Kannan et al., Histidine utilization operon *hut) is upregulated at low temperature in the Antarctic psyhotrophic bacterium *Pseudomonas syringae*, FEMS Microbiology Letters 161, 1998, pp. 7-14.
Accession No. AF326719, Ray et al., (2002).

*Primary Examiner*—James S Ketter
(74) *Attorney, Agent, or Firm*—Foley & Lardner LLP

(57) ABSTRACT

A DNA sequence from the upstream region of cold-inducible hutU gene of the Antarctic Psychrotrophic Bacterium *Pseudomonas syringae*, comprising promoter elements and other regulatory sequences, with unique 'CAAAA' nucleotide sequence at −10 site of multiple transcription start sites and using said promoter to express genes of interest in the said bacterium at temperature as low as 4° C. and using the said bacterium with generation time ranging between two and half to three hours, as a system to produce heat labile proteins of pharmaceutical significance.

30 Claims, 7 Drawing Sheets

Figure 3:
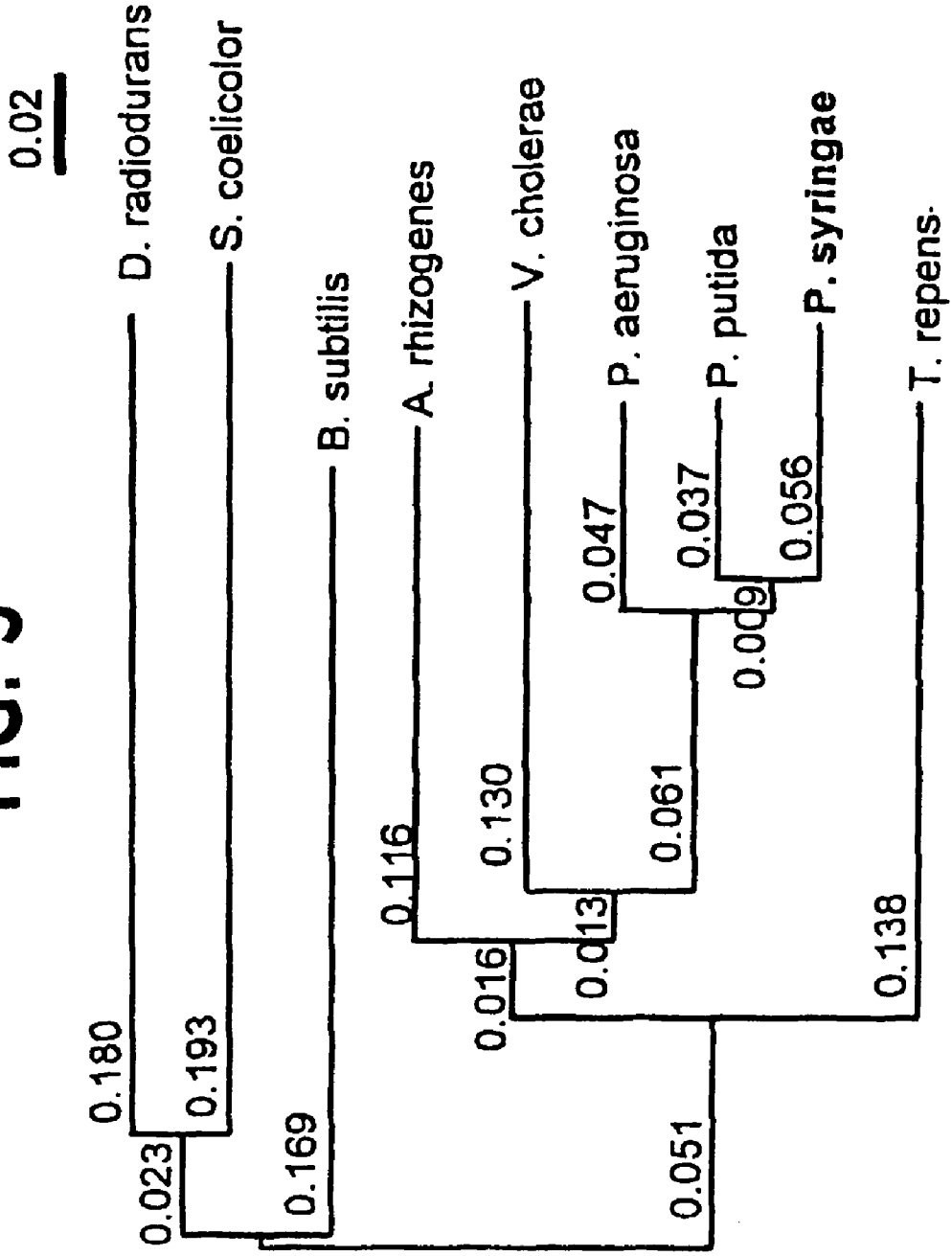

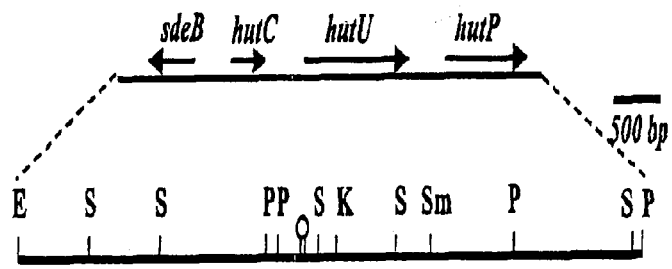
FIG. 1A
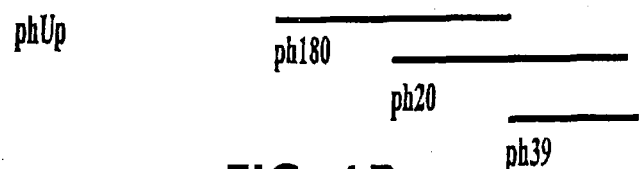
FIG. 1B
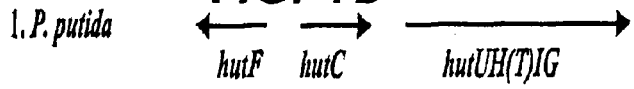
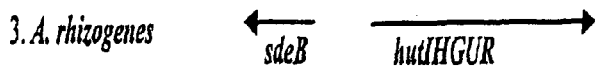
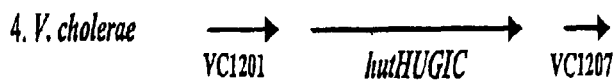
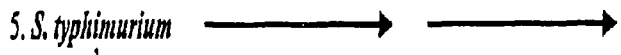
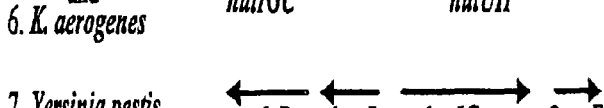
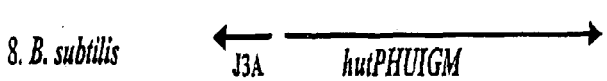
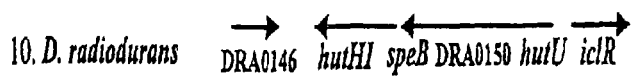

FIG. 2A

```
                            ━━━━━━━━━━━━━━━━━━━━━━━━━━━━━━━━━━━━━━━━━━━━━━━━━
P. SYRINGAE      MTSTTPKSPAAFTRHRDGEIRAARGTQLTAKSWMTEAPLRMLMNNLDPQVAENPTELV   58
P. PUTIDA        MTDNN--------KYRDVEIRAPRGNKLTAKSWLTEAPLRMLMNNLDPQVAENPKELV   50
P. AERUGINOSA    MTTPS--------KFRDIEIRAPRGTTLTAKSWLTEAPLRMLMNNLDPEVAENPRELV   50
V. CHOLERAE      MTQSSAQG---TRLDTQRTIRAPRGTQLRAKSWLTEAPLRMLMNNLDPDVAEHPHALV   55
A. RHIZOGENES    MTNPR--------HNIREIRAPHGSELNAKSWMTEAPLRMLMNNLDPDVAENPHELV   49
T. REPENS        MTDSVS-------KAVARTIRAPHGSELHCANWLIEAAYRMIQNNLDPDVAERPEDLV   51
B. SUBTILIS      MTDVK----------KSIRANRGTELECLGWEQEAVLRMLRNNLDPEVAEKPEDLI   46
S.COELICOLOR     MSG-------------PRPVRAPRGTEPSALGWQQEAALRMLQNNLDPEVAEKPDKLV   45
D. RADIODURANS   MTTHE-----------PRTVRAPRGPHKTAKGWIQEAAKRMLMNNLDPEVAEHPESLV   47
                  *:            ;** :*    .  .* ** **: *****:***.*  *:

━━━━━━━━━━━━━━━━━━━━━━━━━━━━━━━━━━━━━━━━━━━━━━━━━
P. SYRINGAE      VYGGIGRAARNWECYDKIVESLTNLNDDETLLVQSGKPVGVFKTHSNAPRVLIANSNLVP  118
P. PUTIDA        VYGGIGRAARNWECYDKIVETLTRLEDDETLLVQSGKPVGVFKTHSNAPRVLIANSNLVP  110
P. AERUGINOSA    VYGGIGRAARNWECYDRIVETLKQLNDDETLLVQSGKPVGVFKTHANAPRVLIANSNLVP  110
V. CHOLERAE      VYGGIGRAARNWECFDKIVEVLERLEDDQTLLVQSGKPVGVFPTHKNAPRVLIANSNLVP  115
A. RHIZOGENES    VYGGIGRAARTWADFDQIVATLKTLTEEETLLVQSGKPVGVFRTHKDAPRVLIANSNLVP  109
T. REPENS        VYGGIGKAARNWACFEQILRSLQALQPEETLLVQSGKPVGVFRTHADAPRVLIANSNLVP  111
B. SUBTILIS      VYGGIGKAARDWDAFKAIEHSLKTLKNDETLLVQSGKPVGMFRTHPQAPRVLLANSVLVP  106
S.COELICOLOR     VYGGTGKAARDWRSFDAMVRTLRTLKQDETMLVQSGRPVGVMQTHEWAPRVLIANSNLVP  105
D. RADIODURANS   VYGGRGKAARNWEAFDHIVATLDRLENDETLLVQSGKPVAVLRTHEWAPRVLIANSNLVP  107
                 **** *;*** *  :. :     * *  ::*:*****:**.:;  **  *****;*** **.

━━━━━━━━━━━━━━━━━━━━━━━━━━━━━━━━━━━━━━━━━━━━━━━━━
P. SYRINGAE      HWATWEHFNELDAKGLAMYGQMTAGSWINIGSQGIVQGTYETFVEAGRQHYNGSLKGKWV  178
P. PUTIDA        HWAMWEHFNELDAKGLAMYGQMTAGSWIYIGSQGIVQGTYETFVEAGRQHYGGSLKGKWV  170
P. AERUGINOSA    HWATWZHFNELDAKGLAMYGQMTAGSWIYIGSQGIVQGTYETFVEAGRQHYDGNLKGRWV  170
V. CHOLERAE      HWAMWEHFNELDKQGLMMYGQMTAGSWIYIGSQGIVQGTYETFVAVAKKHFNGDAKGRWV  175
A. RHIZOGENES    HWATWDHFNELDKKGLAMYGQMTAGSWIYIGTQGIVQGTYETFVEAGRQHYDGNLKGKWI  169
T. REPENS        HWATWDHFHELDKAGLMMYGQMTAGSWIYIGAQGIVQGTFETFVEAGRKHYNGDLTGKWI  171
B. SUBTILIS      KWADWEHFHELEKKGLMMYGQMTAGSWIYIGSQGILQGTYETFAELARQHFGGSLKGTLT  166
S.COELICOLOR     DWANWEEFRRLEALGLTMYGQMTAGSWIYIGTQGILQGTYETFAAVAAKKFGGTLAGTIT  165
D. RADIODURANS   HWANWETFDKLDQAGLMMYGQMTAGSWIYIGTQGILQGTYETFAGAAQKHFGGSLKGTIT  167
                  .** *; * .*;  ** ************ **:***:***;***,  . .:::.* *

━━━━━━━━━━━━━━━━━━━━━━━━━━━━━━━━━━━━━━━━━━━━━━━━━
P. SYRINGAE      LTAGLGGMGGAQPLAATLAGACSLNIECQQSRIDFRLATRYVDEQALDLDDALVRIAKYT  238
P. PUTIDA        LTAGLGGMGGAQPLAATLAGACSLNIECQQSRIDFRLETRYVDEQATDLDDALVRIAKYT  230
P. AERUGINOSA    LTAGLGGMGGAQPLAATLAGACSLNIECQQSRIDFRLASRYVDEQAKDLDDALARIQRYT  230
V. CHOLERAE      LTGGLGGMGGAQPLAATMAGFSHIAVECDESRIDYRLRTGYVDKKANTLDEALAMIADT-  234
A. RHIZOGENES    LTGGLGGMGGAQPLAAVMAGACCLAVESDETRIDFRLRTRYVDAKAKTLDEALSMIAEWT  229
T. REPENS        LTAGLGGMGGAQPLAGVLAGACVLAVECQESRIDFRLRTRYLDHKAFSVDEALAIIDKAC  231
B. SUBTILIS      LTAGLGGMGGAQPLSVTMNEGVVIAVEVDEKRIDKRIETKYCDRKTASIEEALAWAEEAK  226
S.COELICOLOR     LTAGLGGMGGAQPLAVTMNDGVVICVDCDPRAIDRRIEHHYLDVKADSLDHALQLATEAR  225
D. RADIODURANS   VTAGLGGMGGAQPLAVKLAGGVSITIEIDPTRIRKRLETRYLDEVADNLQDAIARAEGYK  227
                 :*.********:  :    ;   :::  *  *;  **   : *   : ::.*:
                 GXGX₂G----X₁₀----G

━━━━━━━━━━━━━━━━━━━━━━━━━━━━━━━━━━━━━━━━━━━━━━━━━
P. SYRINGAE      AEGKAISIALCGNAAELLPEMVRR----GVRPDMVTDQTSAHDPLNGYLPKGWTWEQYRD  294
P. PUTIDA        AEGKAISIALHGNAAEILPELVKR----GVRPDMVTDQTSAHDPLNGYLPAGWTWEQYRD  286
P. AERUGINOSA    AEGKAISIALLGNAAEILPELVRR----GVRPDMVTDQTSAHDPLNGYLPAGWSWEEYRD  286
V. CHOLERAE      -D-RPISVGLLGNAADIFPELVKR----NITPDVVTDQTSAHDPLNGYLPLGWSMEKAAQ  288
A. RHIZOGENES    AKGEAKSVGLLGNAAEVFPELVKRMKAGGPRPDIVTDQTSAHDPLNGYLPIGWTVAEHKA  289
T. REPENS        KEKRAISVGLLGNAAEILPELVQRAKAGGMKPDIVTDQTSAHDPINGYLPAGWDLARWES  291
B. SUBTILIS      LAGKPLSIALLGNAAEVHHTLLNR----GVKIDIVTDQTSAHDPLIGYVPEGYSLDEADR  282
S.COELICOLOR     DRRKPLSIGVLGNAAELVPQLLAM----GAPIDIVTDQTSAHDPLA-YLPTGIAFEDMAD  280
D. RADIODURANS   AQGVARSIGVQGNAAELVPQLVEM----NWTPDLLTDQTSAHDPMWGYIPPVNADEDAGK  283
                 . :.; ****::    ::     .     *:;********** : *
```

FIG. 2B

```
                    ┌──────────────────────────────────┐  ┌────────┐
P. SYRINGAE     RAVTDPAAVVKAAKASMGEHVEAMLAFQKAGIPTFDYGNNIRQMAKEVGVENAFDFPGFV  354
P. PUTIDA       RAQTEPAAVVKAAKQSMAVHVQAMLDFQKQGVPTFDYGNNIRQMAKEEGVANAFDFPGFV  346
P. AERUGINOSA   RAQTDPAAVVKAAKQSMAVHVRAMLAFQQQGVPTFDYGNNIRQMAKEEGVANAFDFPGFV  346
V. CHOLERAE     MRQQNEAEVVKAAKASMAIQVRAMLDLQTRGAATLDYGNNIRQMALEEGVANAFDFPGFV  348
A. RHIZOGENES   KRETDPKAVEAAARASMXIQVEAMVAFWDAGVPTLDYGNNIRQVAKDEGFENAFAFPGFV  349
T. REPENS       SRQSDPKAVEKAARASMAVHVQAMLDFCHMGIPTVDYGNNIRQVALDEGVKNAFDFPGFV  351
B. SUBTILIS     LRQDTPELYVRLAKQSMKKHVEAMLAFQQKGSIVFDYGNNIRQVAKDEGLENAFDFPGFV  342
S.COELICOLOR    AAAKDPAGFTTRARESMARHVEAMVGFQDAGAEVFDYGNSIRGEAQLAGYDRAFAFPGFV  340
D. RADIODURANS  LRSEHAEEYRQRAYAAMAAHVRAMLELQKRGAVTFDYGNNLRQRAFEAGVEDAFSYPGFV  343
                  *  :*  :*.**:  ;    *   ..****.;*  *    *    **  ;****

┌──────┐  ┌──┐┌─────────┐┌────────────┐
P. SYRINGAE     PAYIRPLECRGVGPFRWVALSGDAEDIYKTDAKVKELIADDAHLHNWLDMARERISFQGL  414
P. PUTIDA       PAYIRPLECRGVGPFRWAALSGEAEDIYKTDAKVKELIPDDAHLHRWLDMARERISFQGL  406
P. AERUGINOSA   PAYIRPLECRGIGPFRWAALSGDPQDIYKTDAKVKQLIPDDAHLHRWLDMARERISFQGL  406
V. CHOLERAE     PAYIRPLECEGIGPFRWAALSGDPEDIYKTDQKVKELIPDNPHLHNWLDMARERIHFQGL  408
A. RHIZOGENES   PAYIRPLECRGIGPFRWAALSGNPEDIYKTDAKVKELLPDNKHLHNWLDMAKERLAFQGL  409
T. REPENS       PAYIRPLECEGKGPFRWALSGDPEDIYKTDAKLKALFPEHTNLHRWLDMAQERIAFQGL  411
B. SUBTILIS     PAYIRPLECEGKGPFRWAALSGDPADIYRTDALLKELFPTNKALHRWIDMAQEKVIFQGL  402
S.COELICOLOR    PAYIRPLECEGKGPFRWAALSGDPADIAKTDKAILDLFPENESLARWIKMAGERVHFQGL  400
D. RADIODURANS  PAFIRDSHCEGRGPFRWVALSGDPQDIYATDKALLELFPEDERLQSWLTYAADQLAFQGL  403
                **.**  **.* *****.****.;.  **  ** ; *:. .    *;  *  :::

┌────────┐  ┌───────┐ ┌──┐    ┌──┐
P. SYRINGAE     PARICWVGLGQRAKLGLAFNEMVRSGELKAPIVIGRDHLDSGSVSSPNRETESMKDGSDA  474
P. PUTIDA       PARICWVGLGLRAKLGLAFNEMVRSGELSAPVVIGRDHLDSGSVSSPNRETEAMRDGSDA  466
P. AERUGINOSA   PARICWVGLGLRAKLGLAFNEMVRTGELSAPIVIGRDHLDSGSVASPNRETEAMQDGSDA  466
V. CHOLERAE     PARICWVGLKDRARLGLAFNEMVKNGELKAPIVIGRDHLDSGSVASPNRETEGMLDGSDA  468
A. RHIZOGENES   PARICWVGLGDRHRLALAFNEMVKNGELSAPVVIGRDHLDSGSVASPNRETEAMKDGSDA  469
T. REPENS       PARICWLGLGERHLAGLAFNEMVRNGELKAPVVIGRDHLDCGSVASPNRETEAMMDGSDA  471
B. SUBTILIS     PSRICWLGYGERKKMGLAINELVRTGELKAPVVIGRDHLDCGSVASPNRETEAMKDGSDA  462
S.COELICOLOR    PARICWLGYGERDKAGERFNDMVASGELAAPIVIGRDHLDCGSVASPYRETEAMLDGSDA  460
D. RADIODURANS  PARICWLGYKERDRAAKLFNDMVKDGRVKAPIVIGRDHLDAGSVASPYRETEAMKDGSDA  463
                *.****.*        , ;*::**  *.: **:*******.***.** ****.* *****

┌──────────────┐┌────┐┌──┐ ┌─────┐
P. SYRINGAE     VSDWPLLNALLNTASGATWVSLHHGGGVGMGFSQHSGMVIVCDGTDEAAERIARVLHNDP  534
P. PUTIDA       VSDWPLLNALLNTAGGATWVSLHHGGGVGMGFSQHSGMVIVCDGTDEAAERIARVLTNDP  526
P. AERUGINOSA   VSDWPLLNALLNTASGATWVSLHHGGGVGMGFSQHSGMVIVCDGSDEAAERIARVLTNDP  526
V. CHOLERAE     VSDWPLLNALLNTAGGATWVSLHHGGGVGMGFSQHSGMVICCDGSDDAAERIARVLHNDP  528
A. RHIZOGENES   VSDWPLLNALLNTASGATWVSLHHGGGVGMGFSQHSGVVICADGSDDAAKRLERVLWNDP  529
T. REPENS       VSDWPLLNALLNTAGGATWVSLHHGGGVGMGFSQHAGVVTVADGTAEADARLSRVLWNDP  531
B. SUBTILIS     VGDWAVLNALVNTAAGASWVSFHHGGGVGMGYSLHAGMVAVADGSELADERLARVLTSDP  522
S.COELICOLOR    IADWPLLNAMVNVASGASWVSLHHGGGVGMGRSIHAGQVTVADGTPLAGEKIRRVLTNDP  520
D. RADIODURANS  VSDWPLLNFGVGIASGASWMSFHHGGGVGLGFSQHSGLVIVADGTDEAAKKLSRALTNDP  523
                :,**.:**   :. *.**:*;*;******* * *:* *..**:  *  :: *.* .**

┌──┐┌────────┐
P. SYRINGAE     ATGVMRHADAGYDIAIDCANEQGLNLPMING--------------------  565
P. PUTIDA       GTGVMRHADAGYDIAIDCAKEQGLDLPMITG---------------------  557
P. AERUGINOSA   GTGVMRHADAGYQVAIDCAKEQGLNLPMITAQR-------------------  559
V. CHOLERAE     ATGVMRHADAGYEIAKRCAQQQKLDLPMLNAELAKLK---------------  565
A. RHIZOGENES   ATGVMRHADAGYDIALDCAKDKGLRLPGILGN--------------------  561
T. REPENS       ATGVMRHADAGYEVARDCARRHELTLPMAKELP-------------------  564
B. SUBTILIS     GMGIIRHADAGYERAVEVAKEQDIIVPMQK----------------------  552
S.COELICOLOR    GMGVIRHVDAGYDIAESVAAERDVRVPMREGDEAHEGDAAHGSGAAREGDGV  572
D. RADIODURANS  GMGVIRHADAGYDHALDVARERGIDLPS-LGIKDHA----------------  558
                . *;;**.****; *  *  ;;  ;*
```

FIG. 6A

```
       PstI
       2961
       ctgcagctga acgacaacag tgaactgctg gaaatcacgg taaccggccg ctgctgtgtg
              hutC OrfII (stop)
       attgagttga gcgggatcta aGCCGCACAT ACACCTCTGT AGGAGCGAGC TTGCTCGCGA
                                                                        →
       GCTCTTGAAT GCGGCCACCA AGAGCTCGCT CCTGCAAGGT TTGAGTCATT GCTGCGCCCC
                ←
         -35                     -10        +1 ↱ 4°C           -35
       ATCTTGTTAC CGAACGCCCT AAAAAGACGC AAAACCCCCG CTTCAGTAAC ATCCCTGCGC +1 ↱ 4°/22°C
       TTTGCCCTTT ACTCCCTGCA AAAATCCTTT CATCCCTCAT CGCCTTGATT TTCGTGCCTT
                                                                  (N)10
       GCAGCTTCGA ATACTTAAAT TTCACGGGCT GATATCGCAC CTTGGCCGCT TACTTGCATA
                ⇓                    SalI
       TGCTTGTATG TACAAGTACA TAAGTGTGCG TCGACCCTCT TGTCCCCGAC GCATCTGCCC
            SD           f-Met (HutU) →
       ATCGCTGAGG ATTACCGTG GACTTCAACT ACCCCTAAAT CGCCAGCTGC GTTTACCCGT
                                 ←---------------------------
                                 KpnI
       CATCGTGATG GTGAAATCCG CGCCGCCCGC GGTACCCAGC TCACTGCCAA AAGCTGGATG
       ACCGAAGCTC CGCTGCGGAT GTTGATGAAC AACCTCGACC CGCAAGTGGC CGAGAACCCG
       ACCGAACTGG TGGTATATGG CGGTATTGGG CGTGCAGCGC
                                                3600
```

FIG. 6B

```
         CGG
        G   C
        T   C
        A   A
       A    A
        G-C
        T-A
        T-A
        C-G
        T-A
        C-G
        G-C
        A-T         ΔG = -16.6 kCal
        G-C
        C-G
TTGCTCG - C T -(69 nt)-Transcription initiation site at 4°C
```

REGULATORY ELEMENTS OF COLD-INDUCIBLE *HUTU* GENE FROM THE ANTARCTIC PSYCHROTROPHIC BACTERIUM *PSEUDOMONAS SYRINGAE*

This application is a continuation application of U.S. patent application Ser. No. 10/349,308, filed on Jan. 23, 2003 now abandoned, which claims the benefit of U.S. Provisional Application No. 60/351,529, filed on Jan. 25, 2002.

FIELD OF THE INVENTION

A DNA sequence from the upstream region of cold-inducible hutU gene of the Antarctic Psychrotrophic Bacterium *Pseudomonas syringae*, comprising promoter elements and other regulatory sequences, with unique 'CAAAA' nucleotide sequence at −10 site of multiple transcription start sites and using said promoter to express genes of interest in the said bacterium at temperature as low as 4° C. and using the said bacterium with generation time ranging between two and half to three hours, as a system to produce heat labile proteins of pharmaceutical significance.

BACKGROUND AND PRIOR ART REFERENCES

Antarctic bacteria provide a useful model system for studying cold adaptation (15, 17, 31, 36). These organisms are generally represented by the psychrotrophs and psychrophiles, which have the ability to grow at 0° C. They can transcribe at this lower temperature both in vitro and in vivo (31). However, nothing much is known about the nature of promoter and regulatory elements from these bacteria or about the mechanism of transcription at lower temperatures. Most of the transcriptional studies thus far have been carried out with only mesophilic bacterium, and the RNA polymerase from these bacteria, including *Escherichia coli*, cannot transcribe at 0° C. A recent study from our laboratory has demonstrated that the RNA polymerase of the Antarctic psychrotrophic bacterium *Pseudomonas syringae* has can transcribe at 0° C. The polymerase from the bacterium was not only active at the low temperature but also could transcribe in vitro preferentially the cold-inducible gene of *E. coli* cspA from a supercoiled template (43). However, absolutely no information is available with regard to the characteristics of promoter sequence such as the −10 and −35 elements from the bacterium for such low temperature specific transcription. Neither is any information available for the in vivo recognition of promoter sequences by RNA polymerase from the cold-adapted *P. syringae*. Therefore, we initially attempted to identify the genes from the Antarctic *P. syringae* that are upregulated at low temperature, with the help of TnJ-mediated random genomic fusions of a prompter-less reporter gene, lacZ (23). One of the fusions that produced at least 10- to 14-fcp,ld more p-galactosida.sc at a low temperature (4° C.) was identified by cloning and sequencing of ca. 450 bp of DNA sequence proximal to the Tn5 insertion site. The fusion was in the hutU gene, which encodes for an enzyme urocanase of the histidine utilization pathway of bacteria (13, 23). A direct assay of urocanase activity from the *P. syringae* and a few more Antarctic *Pseudomonas* species and their comparison with the mesophilic *P. putida* suggested that the hutU gene is unregulated in the psychrotrophs but not in the mesophilic. Therefore, it appeared to us that the hutUgene might be a useful model for investigating the mechanism of gene regulation at low temperatures in the Antarctic bacterium. Accordingly, we cloned and sequenced the DNA encompassing the hut if gene, and its upstream and downstream regions and identified different open reading frames (ORFs) in the region. We also examined transcripts from bacterial cells grown at low (4° C.) and high (22° C.) temperatures by Northern and primer extension analyses, and we identified the transcription start sites and other putative regulatory elements of the hutU gene. Additionally, we compare here the deduced amino acid sequences of the urocanase from the psychrotrophic *P. syringae* and other bacteria, including the mesophilic *P. putida*, in order to examine the possible amino acid substitutions due to a low-temperature adaptation.

OBJECTS OF THE PRESENT INVENTION

The main object of the present invention is to determine the role of promoter and other regulatory elements of antarctic psychrotrophic bacterium *pseudomonas syringae* in expression of proteins under extremely low temperature.

Another object of the present invention is to express the proteins in the said system at fast rate.

Yet another object of the present invention is to determine the transcription initiation site.

Still another object of the present invention is to determine the translation start site.

Still another object of the present invention is to determine sequence homology of regulatory elements.

Still another object of the present invention is to develop a method of producing said sequence from said bacterium.

Still another object of the present invention is to develop a method of using the said sequence to produce heat labile proteins.

Still another object of the present invention is to develop a method of using the said sequence to produce heat labile proteins of pharmaceutical importance.

SUMMARY OF THE PRESENT INVENTION

A DNA sequence from nucleotide 2961 to 3600 of the upstream region of cold-inducible hutU region of the Antarctic Psychrotrophic Bacterium *Pseudomonas syringae* of accession No. AF326719, comprising promoter elements and other regulatory sequences, with unique 'CAAAA' nucleotide sequence at −10 site of multiple transcription start sites and using said promoter to express genes of interest in the said bacterium at temperature as low as 4° C. and using the said bacterium with generation time ranging between two and half to three hours, as a system to produce heat labile proteins of pharmaceutical significance.

DETAILED DESCRIPTION OF THE PRESENT INVENTION

A DNA sequence from nucleotide 2961 to 3600 of the upstream region of cold-inducible hutU region of the Antarctic Psychrotrophic Bacterium *Pseudomonas syringae* of accession No. AF326719, comprising promoter elements and other regulatory sequences, with unique 'CAAAA' nucleotide sequence at −10 site of multiple transcription start sites and using said promoter to express genes of interest in the said bacterium at temperature as low as 4° C. and using the said bacterium with generation time ranging between two and half to three hours, as a system to produce heat labile proteins of pharmaceutical significance.

In an embodiment of the present invention promoter has two transcription initiation sites with low temperature (4° C.), and common low and high temperature (4° C. and 22° C.) specificity.

In yet another embodiment of the present invention the amount of transcripts produced at 4° C. from the hutU gene and hut operon is about 20-fold higher than the amount present at 22° C. during the steady-state growth of the said bacterium.

In still another embodiment of the present invention said gene is inducible upon a downshift of temperature from 22 to 4° C.

In yet another embodiment of the present invention HutU is the Open Reading Frame (ORF) of hutU gene.

In still another embodiment of the present invention amount of mRNAs from the hutU operon increased only about two to three folds on temperature downshift of the said bacterium from 22 to 4° C.

In yet another embodiment of the present invention amount of transcripts produced at 4 and 22° C. or from "cold-shocked" cells after a shift of the culture from 22 to 4° at different time points of 0, 0.5, 1, 2, and 3 hours after that shift.

In still another embodiment of the present invention the amount of mRNAs is at maximum by 2 hours after the shift and decreased subsequently.

In yet another embodiment of the present invention 4° C. specific transcription start site starts with a G, which is 219 nucleotides upstream of the translation initiation codon GTG of the HutU ORF.

In still another embodiment of the present invention the common transcription start site for both low and high temperature is located 39 nucleotides from the low temperature transcription start site.

In yet another embodiment of the present invention the −35 sequence in the promoter region of the 4° C. specific transcript is TGTTAC.

In still another embodiment of the present invention the −35 sequence in the promoter region of the 4 and 22° C. common transcript is CCTGCG.

In yet another embodiment of the present invention the 4° C. specific transcript has second CAAAA sequence at the −15 position.

In still another embodiment of the present invention the second CAAAA nucleotide sequence at low temperature transcript is important for increased expression of the gene at lower temperature.

In yet another embodiment of the present invention sequence at the upstream of the GTG translational start codon of the hutU gene contain HutC repressor binding motif CTTGTATGTACAAG (SEQ ID NO: 1).

In still another embodiment of the present invention catabolite activator protein (CAP) binding sequence, AAGTGTGCGTCGACCCTCTTGT (SEQ ID NO: 2), is located 35 nucleotides upstream of the GTG translation initiation codon of the hutU-ORF.

In yet another embodiment of the present invention said Catabolite Repressor acts as transcriptional roadblock for RNA polymerase.

In still another embodiment of the present invention a conserved "cold-box"-like sequence, TTGATGAACAACC (SEQ ID NO: 3), is located 123 nucleotides downstream of the translation initiation codon of HutU-ORF.

In yet another embodiment of the present invention nitrogen regulatory $\sigma^N$ promoter element, GGCCGCTTACTTGC (SEQ ID NO: 4), is located 81 nucleotides upstream of the translation start site of the HutU-ORF.

In still another embodiment of the present invention said HutU gene can not be expressed in *E. coli* at temperature of about 15° C. and below.

In yet another embodiment of the present invention the Shine-Dalgarno (SD) sequence, GAGGA, is located 12 nucleotides upstream of the translation initiation codon GTG of the hutU ORF.

In still another embodiment of the present invention the cold-shock protein binding sequence, ATTGG, is located 186 nucleotides downstream of the translational initiation codon GTG of hutU ORF.

In yet another embodiment of the present invention regulatory sequence GCGAGCTCTTGAATGCGGCCACCAAGAGCTCGC (SEQ ID NO: 5), having hairpin loop structure is located 70 nucleotides upstream of low temperature transcription start site.

In still another embodiment of the present invention change of free energy ($\Delta G$) for the said loop is about −16.6 kcal.

In yet another embodiment of the present invention said loop functions as a transcription stop signal for the upstream hutC gene.

In still another embodiment of the present invention said loop functions as a regulatory element for transcription of the hutU gene.

Another embodiment of the present invention, a method of cloning and expressing cold-inducible hutU gene from the Antarctic Psychrotrophic Bacterium *Pseudomonas Syringae*, said method comprising steps of:
  a. cloning 2.4 kbp Pst DNA fragment containing hutU gene, and three overlapping fragments containing upstream 3.5 kbp Eco-RI-Kpn I fragment, downstream 2.54 Kbp SalI and 1.2 Kbp Pst I fragments into pUC19,
  b. sequencing the clone, and
  c. expressing the sequence clone.

In yet another embodiment of the present invention expressing gene encoding heat labile proteins of interest using DNA sequence of claim 1, said method comprising introducing said sequence at the upstream region of the gene, and expression the said gene, obtaining protein of interest.

A promoter-fusion study with a Tn5-based promoter probe vector had earlier found that the hutU gene which encodes the enzyme urocanase for histidine utilization pathway is unregulated at a lower temperature (4° C.) in the Antarctic psychrotrophic bacterium *Pseudomonas syringae*. To examine the characteristics of the uroranase gene and its promoter elements from the psychrotrophs, the complete hutU and its upstream region from *P. syringae* were cloned, sequenced, and analyzed in the present study. Northern blot and primer extension analyses suggested that the hutU gene is inducible upon a downshift of temperature (22 to 4° C.) and that there is more than one transcription initiation site. One of the initiation sites was specific to the cells grown at 4° C., which was different from the common initiation sites observed at both 4 and 22° C. Although no typical promoter consensus sequences were observed in the flanking region of the transcription initiation sites, there was a characteristic CAAAA sequence at the −10 position of the promoters. Additionally, the location of the transcription and translation initiation sites suggested that the hutU mRNA contains a long 5'-untranslated region, a characteristic feature of many cold-inducible genes of mesophilic bacteria. A comparison of deduced amino acid sequences of urocanase from various bacteria, including the mesophilic and psychrotrophic *Pseudomonas* sp., suggests that there is a high degree of similarity between the enzymes. The enzyme sequence contains a signature motif ($GXGX_2GX_{10}G$) (SEQ ID NO: 6) of the Rossmann fold for dinucleotide (NAD*) binding and two conserved cysteine residues in and around the active site. The psychrotrophic enzyme, however, has an extended N-terminal end.

MATERIALS AND METHODS

Bacterial strains and growth conditions. The Antarctic psychrotrophic bacterium *P. syringae* Lz4W, which grew optimally at 22° C. was isolated, identified, and maintained as reported earlier (42). Routinely, the culture was grown on antarctic bacterial medium, which contains 0.5% peptone (wt/vol) and 0.2% (wt/vol) yeast extract, at room temperature (22° C.) or at a cold temperature (4° C.) when needed. The £. *coli* cells were grown at 37° C. in Luria-Bertani (LB) medium and maintained on LB agar plates.

DNA manipulation techniques and cloning of hulU gene. The bacterial genomic DNA was prepared by as described previously (32). Isolation of plasmid DNA, restriction endonuclease digestion, ligation. transformation, and agarose gel electrophoretic separation of DNA were carried out as described by Sam-brook et ul. (39).

For cloning of the hutU gene from *P. syringae*, a 522-bp DNA fragment from the plasmid pF43, which contained the hutU proximal region of the promoter fusion clone F43 (23). was used as a probe. Initially, a 2.4-khp ftrl DNA fragment containing the hutU gene was cloned in pUC19 (phlSO). Subsequently, three more overlapping fragments containing the upstream 3.5-kbp EcoRl-Kpnl fragment (phUp) and the downstream 2.54-kbp Sall and 1.2-kb pstI fragments (ph20 and ph39, respectively) were cloned. A total of 6.578 kbp were thus cloned spanning the region (FIG. IA).

DNA sequence analysis. Nucleotide sequence determination were carried out on an automated DNA sequencer (ABI model 377), by using double-stranded plasmid DNAs as a template and ABI PRISM Dye terminator cycle sequencing method (Perkin-Elmer). The BLAST programs (3. 4) were employed for DNA sequence homology search in the NCBI GenBank sequence database (http://www.ncbi.nlm.gov/). PCGENE programs were also used for various DNA and amino acid sequence analyses. Secondary structure prediction analysis of protein was carried out by using the Predict-Protein PHD mail server at EMBL. Heidelberg (predict-HclpfffEMBL-Heidclbcrg.DE), which uses combined evolutionary information and neural networks for structural predictions (34, 35).

The nucleotide sequence reported here has been submitted to Genbank under accession number AF326719.

Isolation nf RNA and Northern analysis. RNA was isolated by hot phenol method (1) from the bacterial cells (optical density at 600 nm of –0.5) grown at 22 and 4° C. For the isolation of RNA from cold-shocked cells, *P. syringae* was initially grown at 22° C. and then shifted to 4° C. and incubated for various time periods before the isolation. Northern hybridization was carried out as described earlier (32) but with the hulU- and hulP-specific probes. Densitometer scanning (Molecular Dynamics) of the autoradiograms was carried out for estimating the fold induction of RNA.

Primer extension analysis. Primer extension analyses were carried out by two methods on the total RNA isolated from 4 and 22° C. grown cells. In the first method (39), a $^{32}$P-end-labeled primer (5'-GGGTAGTTGAAGTCACGGGTA AC-3') (SEQ ID NO: 7) corresponding to the complementary sequence of the putative N-terminal end of the HutU-ORF (–7 to +16 nucleotides with respect to the GTG initiation codon) of *P. syringae* was extended in the presence of Moloney murine leukemia virus reverse transcriptase (Pharmacia). In the second method, the unlabeled primer was extended in the presence of $[\alpha\text{-}^{32}P]$ATP and Moloney murine leukemia virus reverse transcriptase as described earlier (8). Both methods produced similar results, except that the primer-extended products were sharper with less background on the autoradiograms obtained by the second method. DNA sequencing reactions were also carried out with the same primer on the double-stranded DNA template (phlSO) with a Sequenase 2.0 Kit (U.S. Biochemicals) and run in parallel with the primer extended products on an 8 M urea-6% polyacrylamide gel for mapping the transcriptional start points as described previously (39).

Enzyme assays. Urocanase activity was assayed spectrophotometrically by the method of George and Phillips (14). 3-Galactosidase was assayed by the method of Miller (28). Proteins were estimated by the method of Bradford (10).

BRIEF DESCRIPTION OF THE ACCOMPANYING DRAWINGS

FIG. 1 Shows Physical map and the organization of the hutU region of *P. syringae*. (A) A 6.578-kbp DNA from the hutU region of *P. syringae* was sequenced and analyzed by cloning the region on four overlapping DNA restriction fragments (phUp, phlSO, ph20, and ph39) shown below the physical map. Only the major restriction enzyme recognition sites (E, EcoRI: K, Kpnl; P, ft/I: S, Sail; Sm, Smal) are indicated on the physical map. The genes (sdeB, hutC, hutU, and hutP) and their directions of transcription are shown at the top. The putative ORFs. such as SdeB, HutC-ORFI and -ORFII, HutU. and HutP are shown as shaded boxes below the physical map. The incomplete ORF of HutP is indicated as a box with a slope at the C-terminal end. A hairpin structure between HutC and HutU indicates the location of a dyad structure in the DNA sequence. (B) The organization of the genes in the hutU region of a few bacteria identified either by earlier genetic studies or by recent genome sequence analyses are shown for comparison. The directions of transcription are indicated above the genes by arrows. The genes encoding various enzymes involved in histidine utilization (hut) are abbreviated as hutH (for histidase), hutU (for urocanase), hull (for imidazolone propionate hydrolase), hutF (for FIGLUase), huiG (for formylglutamate amidohydrolase), hutT (for inducible histidine/urocanate transporter), hutP (putative transporter with similarity to purine-cytosine permease), hutC orfl (putative re-pressor of hut operon), and hutC orfl (3' downstream ORF of hutC). The unknown ORFs of the hutU region in some bacteria are indicated directly by their ORF identification numbers (e.g., VC1201, VC1207, J3A, SC25.10, SC25.15C, and DRA0146).

FIG. 2 Shows Multiple sequence alignment of the deduced amino acid sequence of urocanase and the predicted secondary structure of the enzyme. The sequences of the hutU genes (the numbers in parentheses are GenBank accession numbers) include: *P. putida* (M33923) (SEQ ID NO: 8), *P. aeruginosa* (AE004923) (SEQ ID NO: 9), *A. rhizogenes* (ABO39932) (SEQ ID NO: 10), *T. repens* (P53385) (SEQ ID NO: 11), *V. cholerae* (AEOO4200) (SEQ ID NO: 12), *P. syringae* (AF326719) (SEQ ID NO: 13), *B. subtilis* (P25503) (SEQ ID NO: 14), *S. coelicolor* A3 (AL354048) (SEQ ID NO: 15), and *D. radiodurans* (AEOO1862) (SEQ ID NO: 16). The CLUSTAL X (1.8) Program was used for the alignment. The amino acids have been shown in single letter code. The characters ("#" and ":") indicate the positions of perfectly conserved amino acids and substitution by similar amino acids, respectively. A period indicates the position is conserved in most organisms. The highly conserved active site of the enzyme (FQGLPARICW) (SEQ ID NO: 17) is shown within a box. Apart from the conserved cysteine within the active-site box, a second conserved cysteine (C-363 of P. syringae corresponding to C-355 of the mesophilic P. putida) that is important for enzyme activity (25) has also been marked. The predicted secondary structure shown above the aligned sequences is based on PHDs (profile fed neural network system) developed by Rost et al. (34, 35) and found at predict-Help(o>EMBL-Heideiberg.DE. The helices have been shown as cylinders, the (3-sheets are indicated as block arrows, and the other structures, including the loops and coils, are appear as thick straight lines. The Rossman fold for dinucleotide binding sequence $GXGX_2G-X_{10}-G$ (SEQ ID NO: 6) (where X is a nonspecific amino acid) has been marked below the aligned sequences. A 3-sheet of "SLNIE" (SEQ ID NO: 21) following the helix of Rossman fold is also highly conserved, which contains an acidic residue (E or D) at the 3' end of the sheet that is generally specific for NAD*. Also note that a predicted short N-terminal helix (aa residues 10 or 13) is present only in P. syringae among the compared organisms.

FIG. 3 Relationship among bacterial urocanases. Similarities between the enzymes have been shown as an unrooted neighbor-joining tree, giving all branch lengths (indicated by numerical values). The tree has been drawn by a neighbor-joining plot of the CLUSTAL X (version 1.8) program. The urocanase sequences of gram-negative bacteria (e.g. P. syringae, P. putida, P. aeruginosa, V. cholerae, and A. rhizogenes) and gram-positive bacteria (e.g., B. subtilis, S. coelicolor, and D. radio-durans) fall into two distinct clusters and may have diverged early in evolution. The only sequence of possible plant origin (33), from T. repens, is closer to the sequence of gram-negative bacteria.

Figure 4:
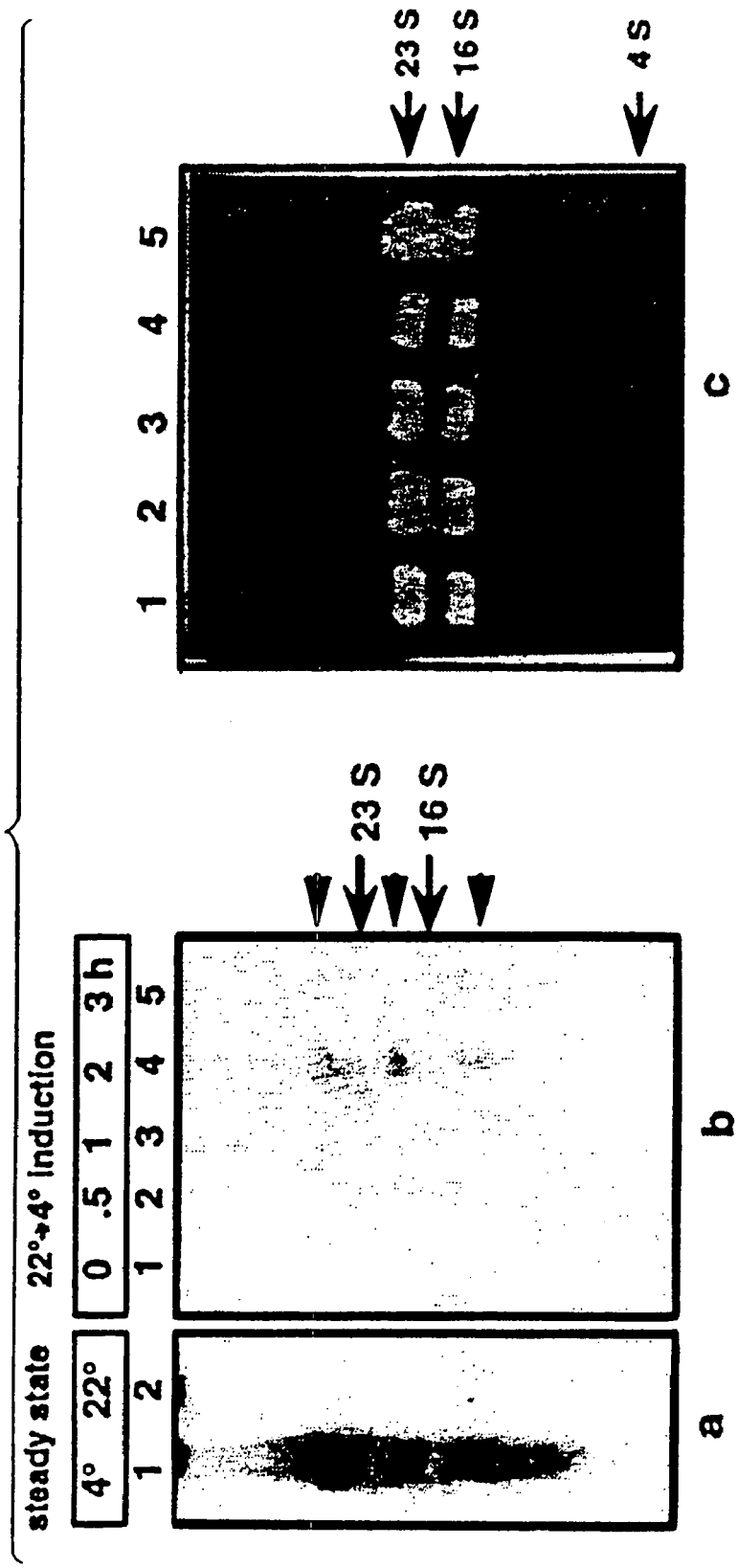

FIG. 4 Northern analysis of transcripts from the HutU region in P. syringae. The RNAs were isolated either from the cells exponentially growing at 4 and 22° C. or from "cold-shocked" cells after a shift of the culture from 22 to 4° C. at different time points (0, 0.5, 1, 2. and 3 h) after that shift. The transcripts from the hutU region are shown at a steady-state level (a) and during the cold-shock induction (b). (c) The RNA loading control (10 u.g) used in the study is shown in a ethidium bromide-stained gel. The positions of the 23S and 16S rRNAs and of the 4S RNA are marked by arrows. The positive signals due to the hybridization of a $^r$P-labeled 2.4-kbp DNA fragment probe spanning all offiutU and part ofhutP (derived from phi80) are marked by arrowheads.

Figure 5:
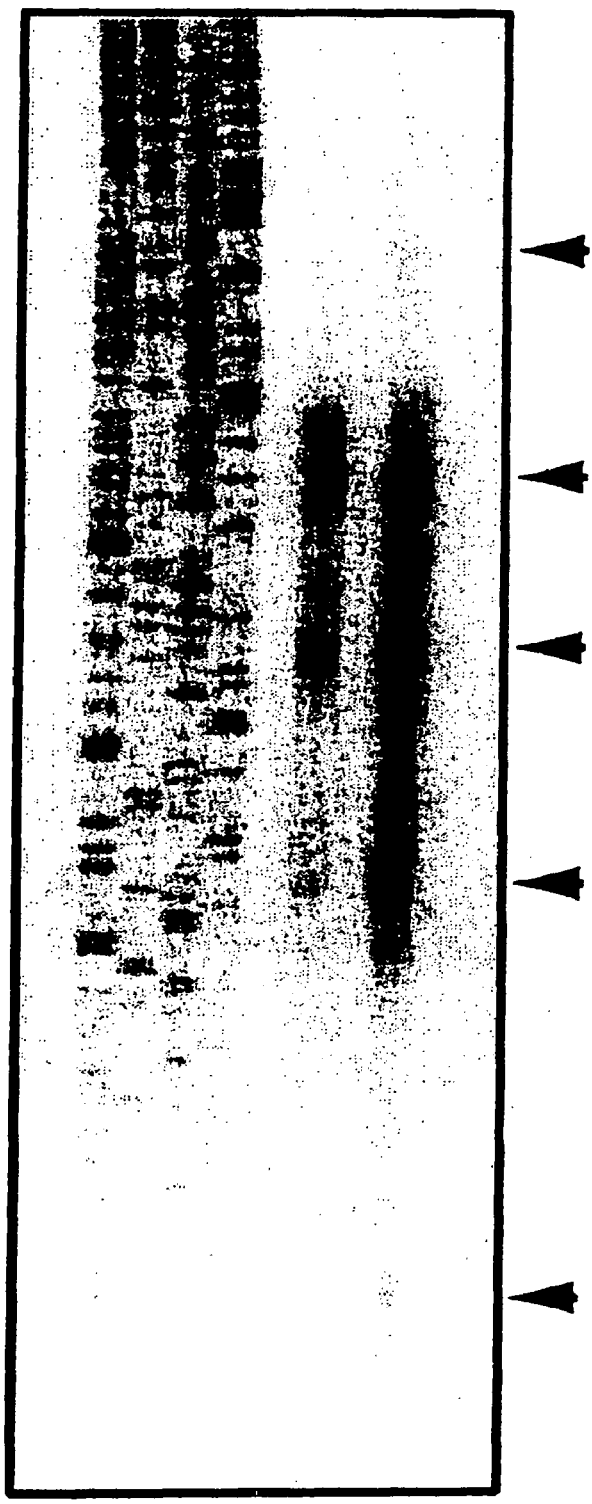

FIG. 5 Primer extension analysis of tuttU transcripts. The RNAs prepared from cells of P. syringae grown at 22 and 4° C. were used for primer extension reactions in the presence of Moloney murine leukemia virus reverse transcriptase and [a-$^{32}$P]ATP, as described in Materials and Methods. The products were analyzed on a sequencing gel (8 M urea-6% polyacrylamide gel electrophoresis) in parallel with the sequencing reaction products (i.e. A, C, G, and T) carried out with the same primer. The major primer-extended products are marked by arrowheads. Note that the two longest primer-extended products were considered for analyzing the promoters in the present study (see FIG. 6). The 4° C. specific longest product was found repeatedly absent in the 22° C. RNA specific reactions. The shortest product (the lowermost arrow) was compatible with a putative ($T^{54}$-specific promoter located in the upstream region of the HutU gene.

FIG. 6. (A) DNA sequence from the upstream region of hutU of P. syringae (SEQ ID NO: 18) containing the promoter elements and other putative regulatory sequences. The dashed arrow shown below the sequence at beginning of the hut U-specific ORF was used for mapping the transcription start sites. The temperature (4° C. and 4 or 22° C.)-specific transcription start sites have been indicated by shaded arrows. The characteristic CAAAA sequence in the promoters is shown within the boxes. The putative ($\sigma^{54}$-specific promoter sequence [GG-($N_{10}$)-GG)] (SEQ ID NO: 26) and the corresponding transcription start site (vertical open arrow) is marked on the sequence. The putative represser HutC binding sequence (CTTGTATGTACAAG) (SEQ ID NO: 19) and CAP binding sequence (AAGTGTGCGTCGACCCTCT-TGT) (SEQ ID NO: 20) have been marked by shaded boxes. The translation initiation codon (GTG), the Shine-Dalgarno (SD) sequence, a putative cold box-like sequence, and a cold-shock protein binding sequence (ATTGG) downstream of the translational initiation site of hutU are marked. The sequence of the 3' end of the orfll of the hutC are underlined and in lowercase. The nucleotide numbers refer to the number in the DNA sequence of the region from P. syringae (accession no. AF326719). (B) Putative regulatory sequence with the potential hairpin structure (SEQ ID NO: 25) in the promoter region of hutU. The location of the hairpin is marked by two opposing arrows below the sequence in panel A.

RESULTS

Cloning and sequence analysis of the hutU region from P. syringae. A 522-bp Tn5-proximal sequence of the hutU promoter fusion clone (F43) of P. syringae (23) was used as a probe to clone the whole of the hutU gene and its upstream and downstream sequences, as described in Materials and Methods. The reported region (6.578 kbp) was cloned on three overlapping DNA fragments (FIG. 1A). The DNA sequence of the region were determined (accession no. AF326719) and analyzed by a BLAST search (3, 4). Four complete and one incomplete ORFs were identified which had homology with the hypothetical sdeB gene homologue of Yersinia pestis (accession no. AL031866), hutC (ORFI), hutC (ORFII), and hutU AQ genes of the but operon of P. putida (2, 13, 19) and the gene yxIA homologue for purine cytosine permease of Bacillus subtilis (accession no. E70081), respectively (FIG. 1). At the level of amino acids, the SdeB homologue (456 amino acids [aa]) was 68% similar to the Y. pestis sequence, and the HutC ORFI (249 aa), HutC ORFII (192 aa), and HutU (565 aa) were 91.63, and 93% similar, respectively, to the P. putida sequences. The ORF of the last gene (yxlA homologue) was incomplete (433 aa versus the complete 457 aa of YxlA), as shown in FIG. 1A. The direction of transcription of the sdeB was opposite to the direction of the other genes. When this gene organization was compared with the organization of but operon of the meso-philic P. putida (19). it was observed that the relative positions oihutC (orfl), hutC (oiflf). and hutU in these two bacteria were identical. The difference was noticed in the hutU downstream region of P. syringae, which was occupied by a homologue to the gene for purine-cytosine permease (henceforth referred to as hutP) of B. subtilis and yeast, instead of the hutH (encoding histidasej found in F putida (FIG. 1B). An electronically submitted data (accession no. AF032970) reveals that a homologue of hutT (encoding an inducible urocanate transporter) is present in the downstream of hutH in P. putida, which was not earlier identified by the genetic study (19, 20). The genome sequence data of P. aeniginosa reveals that the downstream of thshutU gene in the bacterium (FIG. 1B) contains the homologues for both hutP (gene for purine-cytosine permease) and hutT (gene for urocanate transporter). The importance and functional significance of the occurrence of a purine-cytosine permease homologue in the but operon of P. syringae is not clear at present. However, from a comparative analysis of the genes surrounding the hutU region of different bacteria (FIG.

1B), it is apparent that the organization of the genes in the hutU region is quite divergent among various bacteria.

It is also interesting that the genetic data of *P. putida* had earlier established the occurrence of the hutF gene (encoding the enzyme formiminoglutamate iminohydrolase [FIGLUase]) at the upstream of the litit C (19, 20). The hutF gene was shown transcribed divergently from the hutC, similar to the direction of transcription of the sdeB homologues observed in the genome sequence of many gram-negative bacteria, such as *P. syringae, P. aeniginosa. Agrobacterium rhizogenes*. and *Y. pestis* (FIG. IB). Since the DNA sequence for the hutF. gene is not known from *P. putida* or any other bacterium, it remains to be determined whether the sdeB homologue, which also has similarity with the atrazine chlorohydrolases (AtzA, 23% identity; accession no. U55933.1) and the melamine deaminase (TriA, 23% identity, accession no. AF312304.1) of *Pseudomonas* species is the hutF gene of these gram-negative bacteria. In this context, it is interesting that the DNA sequence 108 by upstream of liutC region of *P. putida* (accession no. M33922) contains a beginning of a divergently transcribed ORF (N-terminal 19 aa), which is 93% similar to the first 19 aa of the sedB homologue tjf *P. syringae*. It is also important to note that the hutF is generally thought to be unique for *Pseudomonas* species. The two genes, hutF and hutG, encoding FIGLUase and formylglutamate hydrolase, respectively, are involved in the catalytic conversion of formiminoglutamate (FIGLU) to glutamate and formate by a two-step process in pseudo-monads. This is in contrast to other bacteria, such as *Klebsiella* and *B. subtilis*, where a single enzyme encoded by hutG catalyzes the conversion of FIGLU to glutamate and formamide at the final step of the histidine degradation pathway (19, 26). amino acids, the SdeB homologue (456 amino acids [aa]) was 68% similar to the *Y. pestis* sequence, and the HutC ORFI (249 aa), HutC ORFII (192 aa), and HutU (565 aa) were 91,63, and 93% similar, respectively, to the *P. putida* sequences. The ORF of the last gene (yxlA homologue) was incomplete (433 aa versus the complete 457 aa of YxlA), as shown in FIG. 1A. The direction of transcription of the sdeB was opposite to the direction of the other genes. When this gene organization was compared with the organization of but operon of the mesophilic *P. putida* (19). it was observed that the relative positions of hutC (orff), hutC M. (<<///)·$^{an£}$I Aitft/in these two bacteria were identical. The difference was noticed in the ItutU downstream region of *P. syringae*, which was occupied by a homologue to the gene for purine-cytosine permease (henceforth referred to as hutP) of *B. subtilis* and yeast, instead of the HutH (encoding histidase) found f'. in *P. putida* (FIG. 1B). An electronically submitted data (accession no. AF032970) reveals that a homologue of hutT (encoding an inducible urocanate transporter) is present in the downstream of liutH in *P. putida*, which was not earlier identified by the genetic study (19, 20). The genome sequence data of *P. aeruginosa* reveals that the downstream of the ./wri/gene in the bacterium (FIG. 1B) contains the homologues for both hutP (gene for purine-cytosine permease) and hutT (gene for urocanate transporter). The importance and functional significance of the occurrence of a purine-cytosine permease homologue in the hut operon of *P. syringae* is not clear at present. However, from a comparative analysis of the genes surrounding the hutU region of different bacteria (FIG. 1B), it is apparent that the organization of the genes in the hutU region is quite divergent among various bacteria.

It is also interesting that the genetic data of *P. putida* had earlier established the occurrence of the hutF gene (encoding the enzyme formiminoglutamate iminohydrolase [FIGLUase]) at the upstream of the hutC (19, 20). The hutF gene was shown transcribed divergently from the hutC, similar to the direction of transcription of the sdeB homologues observed in the genome sequence of many gram-negative bacteria, such as *P. syringae, P. aeruginosa. Agrobacterium rhizogenes*. and *Y. pestis* (FIG. IB). Since the DNA sequence for the hutF gene is not known from *P. putida* or any other bacterium, it remains to be determined whether the sdeB homologue, which also has similarity with the atrazine chlorohydrolases (AtzA, 23% identity; accession no. U55933.1) and the melamine deaminase (TriA, 23% identity; accession no. AF312304.1) of *Pseudomonas* species is the hutF gene of these gram-negative bacteria. In this context, it is interesting that the DNA sequence 108 bp upstream of hutC region of *P. putida* (accession no. M33922) contains a beginning of a divergently transcribed ORF (N-terminal 19 aa), which is 93% similar to the first 19 aa of the sedB homologue of *P. syringae*. It is also important to note that the hutF is generally thought to be unique for *Pseudomonas* species. The two genes, hutF and hutG, encoding FIGLUase and formylglutamate hydrolase, respectively, are involved in the catalytic conversion of formiminoglutamate (FIGLU) to glutamate and formate by a two-step process in pseudo-monads. This is in contrast to other bacteria, such as *Klebsiella* and *B. subtilis*, where a single enzyme encoded by hutG catalyzes the conversion of FIGLU to glutamate and formamide at the final step of the histidine degradation pathway (19, 26).

Predictive analysis of the amino acid sequence of urocanase from *P. syringae*. In recent times comparative analyses of proteins from psychrophilic, mesophilic, and thermophilic bacteria have shed new light on the structural adaptability of the enzymes for catalysis at low temperatures and has provided some clues as to their thermal stability (15). Therefore, it was interesting to compare the primary sequence of the urocanase from the psychrotrophic and mesophilic bacteria. Accordingly, the deduced amino acid sequences of the enzyme from the psychrotrophic *P. syringae* and mesophilic *P. putida* were compared (FIG. 2). It was observed that the *P. syringae* enzyme R contains an overall identity of ca. 90% (similarity of 93%) to the *P. putida* enzyme but had an additional 8-aa extension at the N-terminal end (making it 565 aa long). A BLAST search analysis picked up the urocanase homologues from various other bacteria for which the fuitU gene sequences are known. An alignment of the deduced amino acid sequences of the enzyme from these bacteria is shown in FIG. 2. Although the enzyme seems to be quite conserved, it fell into two distinct groups of gram-positive (*B. subtilis, Streptomyces coelicolor*, and *Dt'inococcus radiodurans*) and gram-negative (*P. syringae. P. putida, P. aeruginosa. Vibrio cholerae*. and *A. rhizogenes*)\Q: strains (FIG. 3). The urocanase from the plant (*Trifblium re-repens*) was found clustered with the enzymes from gram-negative bacteria.

From the compositional analyses of the amino acids of urocanase it was apparent that the contents of isoleucine plus leucine (13.1%), the aromatic amino acids (7.2%), and proline (4.4%), which are generally known to change in the psychrophilic enzymes (15), were similar in *P. syringae* and mesophilic *P. putida* (13.28, 7.5, and 4.4%, respectively). A slight increase in the content of serine and threonine (10.4%) was, however, noticed in *P. syringae* when it was compared with the enzymes from *P. putida* and other organisms (7.98 to 9.5%). The arginine content (5.3%), which is known to stabilize the helices, was also marginally lower in *P. syringae* than in the *P. putida* enzyme (5.9%). The *P. syringae* enzyme also contained eight cysteines compared to the seven cysteines of *P. putida* and *P. aeruginosa*. Six of these cysteines are conserved among them and are located in equivalent positions, including the two important cysteines C-410 and C-354 (C-419 and C-363 in *P. syringae*), which were shown to be involved in catalysis and substrate binding, respectively, in the enzyme from *P. putida* (25). Interestingly, the radiotolerant bacterium *D. radiodurans* contains only these two conserved cysteines in the enzyme.

Predictive structural analyses of the urocanase sequence from *P. syringae* exhibited some interesting features (FIG. 2). The enzyme contained a conserved β-α-β structural motif of the dinucleotide binding Rossman fold (GXGX$_2$G-X-G/A) for NAD* binding at the 182- to 198-aa region. A ψ blast analysis suggested that this NAD binding region has structural homology with the similar region of the glutamate dehydroge-nase, including an acidic amino acid residue (E-205 in the case of *P. syringae* urocanase) at the end of the p-strand ($^{201}$SLNIE$^{205}$) (SEQ ID NO: 21) of the β-α-β motif (7). The acidic amino acid residue commonly forms the hydrogen bonds to the adcnine ribose hydroxyls and is generally thought to be an indicator of NAD+ specificity as opposed to the NAD specificity (6, 7). An implication of the identification of the Rossman fold in urocanase would be that, although the loop is similar to that of other NAD+binding proteins, it has to be juxtaposed within a tightly held tertiary or quaternary structural fold of the protein. This is because the exogenously added NAD could not be incorporated into the enzyme in vitro, nor could the coenzyme be dissociated from the protein without irreversible denaturation of the protein (33). The present predictive analysis (FIG. 2) also suggests that the P syringae enzyme contains at the N-terminal end a short α-helix that is absent in other bacteria. Temperature-dependent expression of hutU in *P. syringae*. Northern analyses were carried out to examine the expression of the hutU gene in *P. syringae* at low (4° C.) and high (22° C.) temperatures. It was observed that, during the steady-state growth of the bacterium, the amount of transcripts produced at 4° C. from the hutU gene and but operon was ca. 20-fold higher than the amount present at 22° C. Three transcripts (ca. 7.1, 2.1, and 1.0 kb) hybridized to the probe of 2.4-kbp PstI fragment containing both hutU and hutP genes (FIG. 4a). The hutP-F<specific probe, however, hybridized only to the 7.1-kb transcript (data not shown). Thus, it would appear that the 7.1-kb transcript might represent the polycistronic mRNA, whereas the 2.1- and 1.0-kb transcripts represent the processed and/or degraded product from the operon. The 2.1-kb transcript can potentially encode the full-length hutU gene and therefore might be physiologically important.

Interestingly, upon a temperature downshift of the bacterium from 22 to 4° C., a "cold-shock" response was noticed because the amount of mRNAs from the hut operon increased only about a maximum of two- to threefold after the shift (FIG. 4b). The amount of the mRNAs was at a maximum by 2 after the shift and decreased subsequently. Thus, it appears that the hut operon might have cold-responsive regulatory elements that are known to occur in cold-inducible genes of mesophilic bacteria (12, 29).

Transcription start site and promoter region of the hutU gene of *P. syringae*. Primer extension analyses were carried out to locate the transcription start sites of the hutU gene, with the RNAs isolated from cells of *P. syringae* grown at low (4° C.) and high (22° C.) temperatures (FIG. 5). Among several primer-extended products, the longest product (topmost arrow in FIG. 5) was repeatedly observed only with the RNAs isolated from the cells grown at 4° C. Most of the other extended products were common in cells grown at both low and high temperatures. Based on the longest primer-extended products, the transcription start sites for the low temperature (4° C.) and the common site for both low and high temperatures (4 and 22° C.) were located in the 5' region of the hutU gene (FIG. 6A). Rest F6 of the smaller extended products of the primer extension reactions (FIG. 5) could either represent the true transcription start sites or the processed or degraded ends of the mRNAs.

The low-temperature (4° C.) specific transcript starts with a G, which is 219 nucleotides upstream of the putative translation initiation codon GTG of the HutU ORF. The common transcription start site for both low and high temperatures is located 39 nucleotides downstream from the former start site (FIG. 6A). Thus, the transcripts from the hut operon seems to have a long 5'-untranslated region (5'-UTR) sequence that is a characteristic of the cold-shock genes in mesophilic bacteria, including £. *coli* (12). Upon further examination of the DMA sequences around the transcription start sites, it was observed that the −10 region has a characteristic CAAAA sequence at both temperatures. The −35 sequences in the promoter region of the 4° C. specific and the 4 and 22° C. common transcripts were TGTTAC and CCTGCG, respectively. Interestingly, the promoter region of the 4° C. specific transcript had a second CAAAA sequence at the −15 position; the significance of this, if any, is not yet clear.

The sequence at the upstream of the GTG translational start codon of the hutU gene of *P. syringae* contained a putative HutC repressor binding motif (CTTGTATGTACAAG) (SEQ ID NO: 1), which is slightly different from the sequence observed in *P. putida* and *Klebsiella aerogenes* (2, 40). Interestingly, in the latter organisms this sequence overlaps with the −35 element of the promoter region, in contrast to the case in *P. syringae*, which contains the sequence within the 5'-UTR of the gene (FIG. 6A). It was also observed that a putative nitrogen assimilatory cofactor-binding sequence [ATA-(N$_A$)-TAT] is located overlapped with the HutC-binding motif (41). A putative catabolite activator protein (CAP) binding sequence was also noticed in the downstream of transcription initiation site. The sequence, AAGTGTGC(N$_{fi}$)CCTCTTGT (SEQ ID NO: 22), is located at the 35 nucleotides upstream of the GTG translation inititation codon of the hutU-ORF. In *K. aerogenes* a similar sequence was observed centered around nucleotide −81.5 of the promoter region of hutUH gene cluster (30). Since the CAP binding sequence occurs downstream of the transcription initiation site of *P. syringae*, the catabolite represser in this case could act in theory as a transcriptional roadblock for RNA polymerase. It was also noticed that a putative conserved "cold-box"-like sequence (TTGATGAA-CAACC) (SEQ ID NO: 3), which occurs at the 5' end of the 5'-UTR of the cold-inducible genes of *E. coli*, is located 123 nucleotides downstream of the translation initiation codon of HutU in *P. syringae* (FIG. 6A). Since the location of the cold box is at variance with *E. coli*, any functional significance of the element in *P. syringae* remains to be determined.

A putative nitrogen regulatory σ$^N$ promoter element [GG-(N$_{10}$)-GC] (SEQ ID NO: 23) was also noticed at the 81 nucleotides upstream of the translation start site of the HutU-ORF of *P. syringae*. This is interesting for the observation that the shortest primer-extended product (lowest arrow in FIG. 5) is located very close to the expected position of the transcription start site (at the −13 position rather than at the expected −12 position of the initiation site) of the above σ$^N$ promoter (FIG. 6A). Since histidine is utilized as a source of both carbon and nitrogen in bacteria, the but operon is likely to be regulated by both vegetative (σ$^{70}$ family) and σ$^N$-specific promoters (27), and therefore the occurrence of σ$^N$ promoter might be physiologically important.

Expression of hutU gene in *E. coli*. Since the hutU gene of *P. syringae* contains some common features, including a long 5'-UTR of cold-inducible genes observed in *E. coli*, it was interesting to examine the temperature-dependent expression of the gene in the mesophilic bacterium. The expression of the ImtU gene in *E. coli* was examined by transforming the bacterium with a multicopy plasmid (phlSO) that contained a 2.6-kbp DNA fragment with the structural gene for urocanase and its upstream regulatory sequences from *P. syringae*. The cell extracts prepared from the *£. coli* grown at 37° C. exhibited a modest activity of the enzyme (8.3 u,mol min''' mg of protein"[1]). However, the extracts prepared from the cells grown at a lower temperature (15° C.) did not contain any detectable urocanase activity. Thus, it appears that the hutU gene of *P. syringae* is not expressed in *E. coli* at the lower growth temperature. Whether the lack of expression is due to the absence of cognate regulatory sequences and factors for transcription or to the inability of translation of the hutU mRNA at the lower temperature in *E. coli* remains unknown.

DISCUSSION

The present study was undertaken to determine and analyze the DNA sequences of the hutU gene and its promoter region in order to identify, if possible, the putative regulatory c<< elements for the regulation of the hut operon in the psychrotrophic bacterium *P. syringae*. Additionally, it was thought that an analysis of the deduced amino acid sequence of the enzyme urocanase (the hutU-encoded product) from *P. syringae*, in comparison with the enzyme from mesophilic *P. putida*, might provide the clue to the nature of substitution of amino acids in a cold active enzyme. An earlier study had demonstrated that a urocanase from the psychrophilic *P. putida* A.3.12 could retain, at 0° C., 30% of its maximum activity seen at 30° C. (21). The urocanase in *P. putida* is a homodimer that contains tightly bound NAD* in each subunit, where an intact NAD* is essential for its catalytic reaction. Mechanistically, the enzyme is unique for the fact that the NAD* in this case does not function as a simple redox reagent but as an electrophile for the catalytic addition of water to the urocanate for its conversion into imidazolone propionic acid (7).

Analysis of the genetic organization and promoter region of the hutU in *P. syringae*. The organization of the genes in the hut operon is known to be variable among gram-positive and gram-negative bacteria. The present study indicates that the organization of the hut operon is also variable within the *Pseudomonas* species (FIG. 1B). The analysis also indicates that the nature of the permease gene within the hut operon is variable. For example, Antarctic *P. syringae* has the hutP gene encoding permease belonging to transporter class (TC) 2.A.39.1 (family NCS1), which is different from the hutT encoding a transporter of a different class (TC 2A.1.6.4, family MFS) observed in *P. Putida* (38). The pathogenic *P. aeruginosa* has both the hutP and the hutT within the hut gene cluster. The published genetic study in *P. putida* had earlier failed to locate any permease or transporter gene in the operon (19, 20). A recent study in *Sinorhizobium meliloti* has demonstrated that the histidine degrading hut H gene is linked to a histidine transporter of ATP-binding cassette type (9). Thus, there seems to be a random recruitment of the histidine transporters during the microbial evolution of the histidine degradation pathway.

The regulation of the hut operon, which had mainly been studied in three gram-negative bacteria, including *Salmonella* sp., *K. aerogenes*, and *P. putida*, and one gram-positive bacterium (*B. subtilis*) had also been found to be variable (16, 26). For example, in *B. subtilis* histidine was found to be the main inducer of the operon, while in *P. putida* urocanase was found to be the inducer. Similarly, a positive activator HutP was observed to be the main regulator of the operon in *B. subtilis*, while the repressor HutC was found to be the main negative regulator of the operon in *P. putida*. The regulator of the operon is however, complex in both systems for it is subjected to both carbon catabolite repression and nitrogen metabolite regulation in both of the organisms. The temperature dependent expression of the operon in the cold-adapted bacterium *P. syringae* might further add to the complexity of the regulation of the operon.

In order to investigate the mechanism of temperature dependent regulation of the operon, the promoter region of hutU i.e., the first gene of the operon in *P. syringae*, was been identified here by primer extension analysis. It appears that the mRNA for the hutU gene has a long 5'-UTR that is a characteristic feature of many cold-inducible genes of mesophilic bacteria, including *E. coli*. It also appears that the promoter region of the hutU of *P. syringae* contains various putative cis-acting regulatory elements that have been characterized earlier in mesophilic bacteria. However, the locations of these elements are at variance with the known positions. For example, the repressor HutC binding site, which is known to overlap either with the −35 sequence (e.g. in *P. putide*) or with the region between the −10 and −35 sequences (e.g., in *K. aerogenes*) of the but promoters, has been found at the +143 base (with respect to the 4° C. specific+1 site) and at the +95 base (with respect to the 4 or 22° C. specific common+1 site) region of the 5'-UTR of the hutU gene of *P. syringae* (FIG. 6A). Similarly, a putative binding sequence [ATA-($N_6$)-TAT] (SEQ ID NO: 24) for the positive activator NAC (for nitrogen assimilation control) protein (41) is located downstream of the transcription sites (data not shown). Interestingly, the HutC and NAC binding sites mentioned above overlap each other in *P. syringae*, the significance of which is not yet clear. As pointed out above, the CAP binding sequence is also located downstream of the transcription initiation sites of the operon in the cold-adapted bacterium (FIG. 6A).

The identification of a unique sequence CAAAA at the −10 site of the hutU promoter of *P. syringae* is interesting. This sequence is probably important for the initiation of transcription at both low and high temperatures (e.g. 4 and 22° C.). An extra CAAAA sequence that is observed a half turn away (5 hp) from the DNA helix in the region of the 4° C. specific transcription start site might also be important for increased expression of the gene at lower temperatures. The occurrence of a putative $\sigma^N$ ($\sigma^{54}$) specific promoter sequence, GG-($N_{10}$)-GC (SEQ ID NO: 23), and a corresponding primer-extended product of RNA suggests that the operon might be transcribed by RNA polymerase containing both vegetative sigma and nitrogen regulatory sigma factors, depending upon the environmental signals. The observation of five to six primer-extended products of RNA from the hutU gene might also be a reflection of the complex regulatory process of the operon.

It is also interesting that the putative cold-box sequence observed in the 5'-UTR of the cold-inducible genes of mesophilic *E. coli* is present in the coding region of hutU mRNA of *P. syringae* (FIG. 6). Whether this sequence has any role in *P. syringae* at lower temperatures is a matter of conjecture. Recently, it has been shown in *E. coli* that the Y-box sequence (5'-ATTGG-3') or its inverted repeat 5'-CCAAT-3') might be important for the regulation of cold-inducible genes by an antitermination mechanism (5). In the psychrotrophic *Y. enterocolitica*, the induction of the pnp gene encoding polynucleotide phosphorylase at low temperatures has also been shown to be regulated by the Y-box sequence located 230 bp upstream of the translation start site (18). The promoter region of the low-temperature inducible gene icdII for isocitrate dehydrogenase in the psychrophilic bacterium *Vibrio* sp.

strain AEB1 also contains a CCAAT sequence 2 bp upstream of the −35 site of the promoter that is essential for low-temperature induction (37). The −10 and −35 sequences of the promoter (TAACTA and TTATAG, respectively) in the bacterium were however, not novel in any sense compared to other housekeeping genes. The analysis of the present study, however, failed to show any Y-box sequence in the proper context of the promoter, a 5'-ATTGG-3' sequence observed 185 bp downstream of the GTG initiation codon of the HutU (FIG. 6A).

In order to identify any other putative regulatory elements in the promoter region of hutU, the potential secondary structural elements were also examined. One such structure with a dyad symmetry (AG=−16.6 keal) is located 70 nucleotides upstream of the transcription start site. Such a hairpin loop structure can potentially function as a transcription stop signal for the upstream hutC or as a regulatory element for transcription of the hutU gene. Analysis of the urocanase sequence of *P. syringae*. The deduced amino acid sequence of the urocanase from *P. syringae*, compared with the sequences of the enzyme homologues from other mesophilic bacteria including *K. aerogenes. A. rhizogenes, B. subtilis, S. coelicolor* and *D. radiodurans*, did not show any obvious preference for any specific substitution of amino acids in the protein due to the low-temperature adaptation. The active site of the enzyme in these bacteria (FIG. 2) has an almost identical sequence FQGLPARICW (SEQ ID NO: 17), including the essential cysteine of the mesophilic *P. putida* (25). The two conserved cysteines (C-410 and C-354 of *P. putida*) are present in all of them. All of these enzymes have also a distinct signature motif (GXGX$_2$GX$_{10}$G) (SEQ ID NO: 6) of Rossmann fold, including an equivalent acidic residue at the end of the β-strand of the α/β-fold (FIG. 2). However, multiple alignment of the amino acid sequence suggests that the urocanase has two distinct diverged branches that might be related to the phylogenetic origin of gram-negative and gram-positive bacteria (FIG. 3).

The cold sensitivity of many cold-labile enzymes, including NAD$^+$ specific glutamate dehydrogenase, from various bacteria have been described to the ready dissolution of the monomeric subunits at a lower temperature as a result of weakening hydrophobic bonds (22). Since the hydrophobic bonds stabilize the quaternary structures of proteins and since the enzymes from cold-adapted bacteria have in general reduced hydrophobic interactions to acquire flexibility for functioning at lower temperatures, it might be suicidal for cold active dimeric and oligomeric proteins to adopt a similar strategy. This could be one of the reasons why there are not many substitutions at the level of primary sequence in the dimeric enzyme urocanase from mesophilic *P. putida* and psychrotrophic *P. syringae*. In fact, a recent study shows that the hydrophobic character of the homodimeric enzyme malate dehydrogenase of the psychrophilic bacterium *Aquaspirillium arcticum* is similar to that of the enzyme from the thermophilic bacterium *Thermus flavus* (24). However, three major differences were noticed in the psychrophilic enzyme that were implicated in the efficient catalysts at lower temperature. The differences include (i) an increased relative flexibility at the active-site region of the enzyme; (ii) favorable charge distribution, such as more positive potential around the negatively charged substrate (oxaloacetate) binding site and decreased negative potential around the cofactor NADH-binding site; and (iii) reduced intersubunit ion pairs and decreased buried surface area in the dimeric interface of the enzyme (24). A Similar structure-function study on the urocanase of *P. syringae* would be useful to substantive the generality of these findings.

In conclusion, the present study shows that the −10 and −35 characteristics of the promoter in *P. syringae* are unique. The occurrence of multiple in CAAAA might be important for low-temperature melting of the promoter. The present study also reflects the possible complexity and uniqueness of regulation in the operon of *P. syringae* due to the presence of many putative regulatory cis elements that are located downstream rather than in the usual location upstream of the transcription start site. The present study also identifies two distinct clusters of urocanase sequences among the bacteria that might be related to their origin or lineage. The identification of a Rossmann told for NAD$^+$ binding is also important for future modeling of the enzyme since this site is presumed to be different from other NAD-requiring enzymes for its inaccessibility without denaturation of the urocanase.

The invention claimed is:

1. A method of cloning and expressing the cold-inducible hutU gene from an Antarctic Psychotropic Bacterium *Pseudomonas syringae*, said method comprising the steps of:
   a. cloning a 2.4 kbp Pst DNA fragment containing the hutU gene, and three overlapping fragments containing an upstream 3.5 kbp Eco-R1-Kpn 1 fragment, a downstream 2.54 Kbp SalI and a 1.2 Kbp pstI fragments into pUC19, b. sequencing the clone, and c. expressing the sequenced clone in the Antarctic Psychotropic Bacterium *Pseudomonas syringae;* wherein the fragments comprise a DNA sequence (SEQ. ID No.: 18) from nucleotide 2961 to 3600 of the upstream region of the cold-inducible hutU gene, wherein said DNA sequence comprises a promoter and other regulatory sequences with a CAAAA nucleotide sequence at −10 site of multiple transcription initiation sites.

2. The method of claim 1, wherein said promoter has two transcription initiation sites, wherein one site has a low temperature (4° C.) specificity, the other site has a common low and high temperature (4° C. and 22° C.) specificity.

3. The method of claim 1, wherein the amount of transcripts produced at 4° C. from the hutU gene and but operon is about 20-fold higher than the amount present at 22° C. during the steady-state growth of the said bacterium.

4. The method of claim 1, wherein said gene is inducible upon a downshift of temperature from 22° C. to 4° C.

5. The method of claim 1, wherein HutU is the Open Reading Frame (ORF) of hutU gene.

6. The method of claim 1, wherein the amount of mRNAs from the hutU operon increased only about two to three folds on temperature downshift of the said bacterium from 22° C. to 4° C.

7. The method of claim 1, wherein the amount of transcripts produced at 4° C. and 22° C. or from "cold-shocked" cells after a shift of the culture from 22° C. to 4° C. are measured at different time points of 0, 0.5, 1, 2, and 3 hours after that shift.

8. The method of claim 7 wherein the amount of mRNAs is at maximum by 2 hours after the shift and decreased subsequently.

9. The method of claim 8, wherein the 4° C. specific transcription initiation site starts with a G, which is 219 nucleotides upstream of the translation initiation codon GTG of the hutU ORF.

10. The method of claim 1, wherein the transcription initiation site specific for both low and high temperature is located 39 nucleotides from the low temperature transcription start site.

11. The method of claim 2, wherein the −35 sequence in the promoter region of the 4° C. specific transcript is TGTTAC.

12. The method of claim 2, wherein the −35 sequence in the promoter region of the 4° C. and 22° C. common transcript is CCTGCG.

13. The method of claim 2, wherein the 4° C. specific transcript has a second CAAAA sequence at the −15 position.

14. The method of claim 13, wherein the second CAAAA nucleotide sequence at low temperature transcript is important for increased expression of the gene at lower temperature.

15. The method of claim 1, wherein said DNA sequence comprises a sequence at the upstream of the GTG translational start codon of the hutU gene which contains a HutC repressor binding motif CTTGTATGTACAAG (SEQ ID NO: 1).

16. The method of claim 1, wherein said DNA sequence comprises a catabolite activator protein (CAP) binding sequence, AAGTGTGCGTCGACCCTCTTGT (SEQ ID NO: 2), which is located 35 nucleotides upstream of the GTG translation initiation codon of the hutU-ORF.

17. The method of claim 16, wherein said Catabolite Repressor acts as transcriptional roadblock for RNA polymerase.

18. The method of claim 1, wherein said DNA sequence comprises a conserved "coldbox"-like sequence, TTGATGAACAACC (SEQ ID NO: 3), which is located 123 nucleotides downstream of the translation initiation codon of the hutU-ORF.

19. The method of claim 1, wherein said DNA sequence comprises a nitrogen regulatory $\sigma^N$ promoter element, GGCCGCTTACTTGC (SEQ ID NO: 4), which is located 81 nucleotides upstream of the translation start site of the hutU-ORF.

20. The method of claim 1, wherein said DNA sequence comprises a Shine-Dalgarno (SD) sequence, GAGGA, which is located 12 nucleotides upstream of the translation initiation codon GTG of the hutU-ORF.

21. The method of claim 1, wherein said DNA sequence comprises a cold-shock protein binding sequence, ATTGG, is located 186 nucleotides downstream of the translational initiation codon GTG of the hutU-ORF.

22. The method of claim 1, wherein said DNA sequence comprises a regulatory sequence GCGAGCTCTTGAATGCGGCCACCAAGAGCTCGC (SEQ ID NO: 5), having hairpin loop structure is located 70 nucleotides upstream of low temperature transcription start site.

23. The method of claim 22, wherein the change of free energy ($\Delta G$) for the said loop is about −16.6 kcal.

24. The method of claim 22, wherein said loop functions as a transcription stop signal for the upstream hutC gene.

25. The method of claim 22 wherein, said loop functions as a regulatory element for transcription of the hutU gene.

26. A method of expressing a gene of interest using a DNA sequence (SEQ. ID No.: 18) from nucleotide 2961 to 3600 of the upstream region of the cold-inducible hutU gene in an Antarctic Psychotropic Bacterium *Pseudomonas Syringae* at a temperature as low as 4° C., comprising
   introducing said sequence to the upstream region of the gene, expressing the said gene, and obtaining the protein;
   wherein said DNA sequence comprises a promoter and other regulatory sequences with a CAAAA nucleotide sequence at −10 site of multiple transcription initiation sites.

27. The method of claim 26, wherein the gene of interest encodes a heat labile protein.

28. An isolated DNA sequence comprising SEQ. ID No: 18, which is from nucleotide 2961 to 3600 of the upstream region of cold-inducible hutU gene of the Antarctic Psychrotrophic Bacterium *Pseudomonas syringae*, said sequence comprising promoter elements and other regulatory sequences, with unique CAAAA nucleotide sequence at −10 site of multiple transcription start sites, wherein
   said isolated DNA sequence is operably linked to a gene of interest, allowing the expression of said gene in the Psychrotrophic Bacterium *Pseudomonas syringae*.

29. The sequence as claimed in claim 28 wherein, said promoter has two transcription initiation sites with low temperature (4° C.) specificity, and common low and high temperature (4° C. and 22° C.) specificity.

30. The sequence as claimed in claim 28, wherein the 4° C. specific transcript has a second CAAAA sequence at the −15 position.

* * * * *

SEQUENCE LISTING

```
<160> NUMBER OF SEQ ID NOS: 26

<210> SEQ ID NO 1
<211> LENGTH: 14
<212> TYPE: DNA
<213> ORGANISM: Pseudomonas syringae

<400> SEQUENCE: 1
cttgtatgta caag                                                        14

<210> SEQ ID NO 2
<211> LENGTH: 22
<212> TYPE: DNA
<213> ORGANISM: Pseudomonas syringae

<400> SEQUENCE: 2
aagtgtgcgt cgaccctctt gt                                               22

<210> SEQ ID NO 3
<211> LENGTH: 13
```

-continued

```
<212> TYPE: DNA
<213> ORGANISM: Pseudomonas syringae

<400> SEQUENCE: 3
ttgatgaaca acc                                                          13

<210> SEQ ID NO 4
<211> LENGTH: 14
<212> TYPE: DNA
<213> ORGANISM: Pseudomonas syringae

<400> SEQUENCE: 4
ggccgcttac ttgc                                                         14

<210> SEQ ID NO 5
<211> LENGTH: 33
<212> TYPE: DNA
<213> ORGANISM: Pseudomonas syringae

<400> SEQUENCE: 5
gcgagctctt gaatgcggcc accaagagct cgc                                    33

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence:
      Illustrative signature motif
<220> FEATURE:
<221> NAME/KEY: MOD_RES
<222> LOCATION: (2)
<223> OTHER INFORMATION: Non-specific amino acid
<220> FEATURE:
<221> NAME/KEY: MOD_RES
<222> LOCATION: (4)..(5)
<223> OTHER INFORMATION: Non-specific amino acid
<220> FEATURE:
<221> NAME/KEY: MOD_RES
<222> LOCATION: (7)..(16)
<223> OTHER INFORMATION: Non-specific amino acid

<400> SEQUENCE: 6

Gly Xaa Gly Xaa Xaa Gly Xaa Xaa Xaa Xaa Xaa Xaa Xaa Xaa Xaa
 1               5                  10                  15

Gly

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 7
gggtagttga agtcacgggt aac                                               23

<210> SEQ ID NO 8
<211> LENGTH: 557
<212> TYPE: PRT
<213> ORGANISM: Pseudomonas putida

<400> SEQUENCE: 8

Met Thr Asp Asn Asn Lys Tyr Arg Asp Val Glu Ile Arg Ala Pro Arg
 1               5                  10                  15

Gly Asn Lys Leu Thr Ala Lys Ser Trp Leu Thr Glu Ala Pro Leu Arg
```

-continued

```
                  20                  25                  30
        Met Leu Met Asn Asn Leu Asp Pro Gln Val Ala Glu Asn Pro Lys Glu
                        35                  40                  45

Leu Val Val Tyr Gly Gly Ile Gly Arg Ala Ala Arg Asn Trp Glu Cys
                    50                  55                  60

Tyr Asp Lys Ile Val Glu Thr Leu Thr Arg Leu Glu Asp Asp Glu Thr
         65                  70                  75                  80

Leu Leu Val Gln Ser Gly Lys Pro Val Gly Val Phe Lys Thr His Ser
                            85                  90                  95

Asn Ala Pro Arg Val Leu Ile Ala Asn Ser Asn Leu Val Pro His Trp
                        100                 105                 110

Ala Asn Trp Glu His Phe Asn Glu Leu Asp Ala Lys Gly Leu Ala Met
                    115                 120                 125

Tyr Gly Gln Met Thr Ala Gly Ser Trp Ile Tyr Ile Gly Ser Gln Gly
                130                 135                 140

Ile Val Gln Gly Thr Tyr Glu Thr Phe Val Ala Gly Arg Gln His
        145                 150                 155                 160

Tyr Gly Gly Ser Leu Lys Gly Lys Trp Val Leu Thr Ala Gly Leu Gly
                        165                 170                 175

Gly Met Gly Gly Ala Gln Pro Leu Ala Ala Thr Leu Ala Gly Ala Cys
                    180                 185                 190

Ser Leu Asn Ile Glu Cys Gln Gln Ser Arg Ile Asp Phe Arg Leu Glu
                195                 200                 205

Thr Arg Tyr Val Asp Glu Gln Ala Thr Asp Leu Asp Asp Ala Leu Val
            210                 215                 220

Arg Ile Ala Lys Tyr Thr Ala Glu Gly Lys Ala Ile Ser Ile Ala Leu
        225                 230                 235                 240

His Gly Asn Ala Ala Glu Ile Leu Pro Glu Leu Val Lys Arg Gly Val
                        245                 250                 255

Arg Pro Asp Met Val Thr Asp Gln Thr Ser Ala His Asp Pro Leu Asn
                    260                 265                 270

Gly Tyr Leu Pro Ala Gly Trp Thr Trp Glu Gln Tyr Arg Asp Arg Ala
                275                 280                 285

Gln Thr Glu Pro Ala Ala Val Val Lys Ala Ala Lys Gln Ser Met Ala
            290                 295                 300

Val His Val Gln Ala Met Leu Asp Phe Gln Lys Gln Gly Val Pro Thr
        305                 310                 315                 320

Phe Asp Tyr Gly Asn Asn Ile Arg Gln Met Ala Lys Glu Glu Gly Val
                        325                 330                 335

Ala Asn Ala Phe Asp Phe Pro Gly Phe Val Pro Ala Tyr Ile Arg Pro
                    340                 345                 350

Leu Phe Cys Arg Gly Val Gly Pro Phe Arg Trp Ala Ala Leu Ser Gly
                355                 360                 365

Glu Ala Glu Asp Ile Tyr Lys Thr Asp Ala Lys Val Lys Glu Leu Ile
            370                 375                 380

Pro Asp Asp Ala His Leu His Arg Trp Leu Asp Met Ala Arg Glu Arg
        385                 390                 395                 400

Ile Ser Phe Gln Gly Leu Pro Ala Arg Ile Cys Trp Val Gly Leu Gly
                        405                 410                 415

Leu Arg Ala Lys Leu Gly Leu Ala Phe Asn Glu Met Val Arg Ser Gly
                    420                 425                 430

Glu Leu Ser Ala Pro Val Val Ile Gly Arg Asp His Leu Asp Ser Gly
                435                 440                 445
```

```
Ser Val Ser Ser Pro Asn Arg Glu Thr Glu Ala Met Arg Asp Gly Ser
    450                 455                 460

Asp Ala Val Ser Asp Trp Pro Leu Leu Asn Ala Leu Leu Asn Thr Ala
465                 470                 475                 480

Gly Gly Ala Thr Trp Val Ser Leu His His Gly Gly Val Gly Met
                485                 490                 495

Gly Phe Ser Gln His Ser Gly Met Val Ile Val Cys Asp Gly Thr Asp
                500                 505                 510

Glu Ala Ala Glu Arg Ile Ala Arg Val Leu Thr Asn Asp Pro Gly Thr
            515                 520                 525

Gly Val Met Arg His Ala Asp Ala Gly Tyr Asp Ile Ala Ile Asp Cys
        530                 535                 540

Ala Lys Glu Gln Gly Leu Asp Leu Pro Met Ile Thr Gly
545                 550                 555
```

<210> SEQ ID NO 9
<211> LENGTH: 559
<212> TYPE: PRT
<213> ORGANISM: Pseudomonas aeruginosa

<400> SEQUENCE: 9

```
Met Thr Thr Pro Ser Lys Phe Arg Asp Ile Glu Ile Arg Ala Pro Arg
  1               5                  10                  15

Gly Thr Thr Leu Thr Ala Lys Ser Trp Leu Thr Glu Ala Pro Leu Arg
                20                  25                  30

Met Leu Met Asn Asn Leu Asp Pro Glu Val Ala Glu Asn Pro Arg Glu
            35                  40                  45

Leu Val Val Tyr Gly Gly Ile Gly Arg Ala Ala Arg Asn Trp Glu Cys
        50                  55                  60

Tyr Asp Arg Ile Val Glu Thr Leu Lys Gln Leu Asn Asp Asp Glu Thr
 65                  70                  75                  80

Leu Leu Val Gln Ser Gly Lys Pro Val Gly Val Phe Lys Thr His Ala
                 85                  90                  95

Asn Ala Pro Arg Val Leu Ile Ala Asn Ser Asn Leu Val Pro His Trp
                100                 105                 110

Ala Thr Trp Glu His Phe Asn Glu Leu Asp Ala Lys Gly Leu Ala Met
            115                 120                 125

Tyr Gly Gln Met Thr Ala Gly Ser Trp Ile Tyr Ile Gly Ser Gln Gly
        130                 135                 140

Ile Val Gln Gly Thr Tyr Glu Thr Phe Val Glu Ala Gly Arg Gln His
145                 150                 155                 160

Tyr Asp Gly Asn Leu Lys Gly Arg Trp Val Leu Thr Ala Gly Leu Gly
                165                 170                 175

Gly Met Gly Gly Ala Gln Pro Leu Ala Ala Thr Leu Ala Gly Ala Cys
            180                 185                 190

Ser Leu Asn Ile Glu Cys Gln Gln Ser Arg Ile Asp Phe Arg Leu Arg
        195                 200                 205

Ser Arg Tyr Val Asp Glu Gln Ala Lys Asp Leu Asp Asp Ala Leu Ala
    210                 215                 220

Arg Ile Gln Arg Tyr Thr Ala Glu Gly Lys Ala Ile Ser Ile Ala Leu
225                 230                 235                 240

Leu Gly Asn Ala Ala Glu Ile Leu Pro Glu Leu Val Arg Arg Gly Val
                245                 250                 255

Arg Pro Asp Met Val Thr Asp Gln Thr Ser Ala His Asp Pro Leu Asn
```

-continued

```
                260                 265                 270
Gly Tyr Leu Pro Ala Gly Trp Ser Trp Glu Tyr Arg Asp Arg Ala
        275                 280                 285
Gln Thr Asp Pro Ala Ala Val Val Lys Ala Ala Lys Gln Ser Met Ala
290                 295                 300
Val His Val Arg Ala Met Leu Ala Phe Gln Gln Gly Val Pro Thr
305                 310                 315                 320
Phe Asp Tyr Gly Asn Asn Ile Arg Gln Met Ala Lys Glu Glu Gly Val
                325                 330                 335
Ala Asn Ala Phe Asp Phe Pro Gly Phe Val Pro Ala Tyr Ile Arg Pro
            340                 345                 350
Leu Phe Cys Arg Gly Ile Gly Pro Phe Arg Trp Ala Ala Leu Ser Gly
            355                 360                 365
Asp Pro Gln Asp Ile Tyr Lys Thr Asp Ala Lys Val Lys Gln Leu Ile
            370                 375                 380
Pro Asp Asp Ala His Leu His Arg Trp Leu Asp Met Ala Arg Glu Arg
385                 390                 395                 400
Ile Ser Phe Gln Gly Leu Pro Ala Arg Ile Cys Trp Val Gly Leu Gly
                405                 410                 415
Leu Arg Ala Lys Leu Gly Leu Ala Phe Asn Glu Met Val Arg Thr Gly
            420                 425                 430
Glu Leu Ser Ala Pro Ile Val Ile Gly Arg Asp His Leu Asp Ser Gly
            435                 440                 445
Ser Val Ala Ser Pro Asn Arg Glu Thr Glu Ala Met Gln Asp Gly Ser
        450                 455                 460
Asp Ala Val Ser Asp Trp Pro Leu Leu Asn Ala Leu Leu Asn Thr Ala
465                 470                 475                 480
Ser Gly Ala Thr Trp Val Ser Leu His His Gly Gly Val Gly Met
                485                 490                 495
Gly Phe Ser Gln His Ser Gly Met Val Ile Val Cys Asp Gly Ser Asp
                500                 505                 510
Glu Ala Ala Glu Arg Ile Ala Arg Val Leu Thr Asn Asp Pro Gly Thr
            515                 520                 525
Gly Val Met Arg His Ala Asp Ala Gly Tyr Gln Val Ala Ile Asp Cys
        530                 535                 540
Ala Lys Glu Gln Gly Leu Asn Leu Pro Met Ile Thr Ala Gln Arg
545                 550                 555

<210> SEQ ID NO 10
<211> LENGTH: 561
<212> TYPE: PRT
<213> ORGANISM: Agrobacterium rhizogenes

<400> SEQUENCE: 10

Met Thr Asn Pro Arg His Asn Ile Arg Glu Ile Arg Ala Pro His Gly
1               5                   10                  15
Ser Glu Leu Asn Ala Lys Ser Trp Met Thr Glu Ala Pro Leu Arg Met
                20                  25                  30
Leu Met Asn Asn Leu Asp Pro Asp Val Ala Glu Asn Pro His Glu Leu
            35                  40                  45
Val Val Tyr Gly Gly Ile Gly Arg Ala Ala Arg Thr Trp Ala Asp Phe
        50                  55                  60
Asp Gln Ile Val Ala Thr Leu Lys Thr Leu Thr Glu Glu Glu Thr Leu
65                  70                  75                  80
```

-continued

Leu Val Gln Ser Gly Lys Pro Val Gly Val Phe Arg Thr His Lys Asp
            85                  90                  95

Ala Pro Arg Val Leu Ile Ala Asn Ser Asn Leu Val Pro His Trp Ala
            100                 105                 110

Thr Trp Asp His Phe Asn Glu Leu Asp Lys Lys Gly Leu Ala Met Tyr
            115                 120                 125

Gly Gln Met Thr Ala Gly Ser Trp Ile Tyr Ile Gly Thr Gln Gly Ile
        130                 135                 140

Val Gln Gly Thr Tyr Glu Thr Phe Val Glu Ala Gly Arg Gln His Tyr
145                 150                 155                 160

Asp Gly Asn Leu Lys Gly Lys Trp Ile Leu Thr Gly Leu Gly Gly
            165                 170                 175

Met Gly Gly Ala Gln Pro Leu Ala Ala Val Met Ala Gly Ala Cys Cys
        180                 185                 190

Leu Ala Val Glu Ser Asp Glu Thr Arg Ile Asp Phe Arg Leu Arg Thr
            195                 200                 205

Arg Tyr Val Asp Ala Lys Ala Lys Thr Leu Asp Glu Ala Leu Ser Met
        210                 215                 220

Ile Ala Glu Trp Thr Ala Lys Gly Glu Ala Lys Ser Val Gly Leu Leu
225                 230                 235                 240

Gly Asn Ala Ala Glu Val Phe Pro Glu Leu Val Lys Arg Met Lys Ala
            245                 250                 255

Gly Gly Pro Arg Pro Asp Ile Val Thr Asp Gln Thr Ser Ala His Asp
        260                 265                 270

Pro Leu Asn Gly Tyr Leu Pro Ile Gly Trp Thr Val Ala Glu His Lys
            275                 280                 285

Ala Lys Arg Glu Thr Asp Pro Lys Ala Val Glu Ala Ala Arg Ala
        290                 295                 300

Ser Met Lys Ile Gln Val Glu Ala Met Val Ala Phe Trp Asp Ala Gly
305                 310                 315                 320

Val Pro Thr Leu Asp Tyr Gly Asn Asn Ile Arg Gln Val Ala Lys Asp
            325                 330                 335

Glu Gly Phe Glu Asn Ala Phe Ala Phe Pro Gly Phe Val Pro Ala Tyr
        340                 345                 350

Ile Arg Pro Leu Phe Cys Arg Gly Ile Gly Pro Phe Arg Trp Ala Ala
            355                 360                 365

Leu Ser Gly Asn Pro Glu Asp Ile Tyr Lys Thr Asp Ala Lys Val Lys
        370                 375                 380

Glu Leu Leu Pro Asp Asn Lys His Leu His Asn Trp Leu Asp Met Ala
385                 390                 395                 400

Lys Glu Arg Ile Ala Phe Gln Gly Leu Pro Ala Arg Ile Cys Trp Val
            405                 410                 415

Gly Leu Gly Asp Arg His Arg Leu Ala Leu Ala Phe Asn Glu Met Val
        420                 425                 430

Lys Asn Gly Glu Leu Ser Ala Pro Val Val Ile Gly Arg Asp His Leu
            435                 440                 445

Asp Ser Gly Ser Val Ala Ser Pro Asn Arg Glu Thr Glu Ala Met Lys
        450                 455                 460

Asp Gly Ser Asp Ala Val Ser Asp Trp Pro Leu Leu Asn Ala Leu Leu
465                 470                 475                 480

Asn Thr Ala Ser Gly Ala Thr Trp Val Ser Leu His His Gly Gly Gly
            485                 490                 495

Val Gly Met Gly Phe Ser Gln His Ser Gly Val Val Ile Cys Ala Asp

```
                        500                 505                 510
Gly Ser Asp Asp Ala Ala Lys Arg Leu Glu Arg Val Leu Trp Asn Asp
            515                 520                 525
Pro Ala Thr Gly Val Met Arg His Ala Asp Ala Gly Tyr Asp Ile Ala
        530                 535                 540
Leu Asp Cys Ala Lys Asp Lys Gly Leu Arg Leu Pro Gly Ile Leu Gly
545                 550                 555                 560
Asn

<210> SEQ ID NO 11
<211> LENGTH: 564
<212> TYPE: PRT
<213> ORGANISM: Trifolium repens

<400> SEQUENCE: 11

Met Thr Asp Ser Val Ser Lys Ala Val Ala Arg Thr Ile Arg Ala Pro
  1               5                  10                  15
His Gly Ser Glu Leu His Cys Ala Asn Trp Leu Ile Glu Ala Ala Tyr
             20                  25                  30
Arg Met Ile Gln Asn Asn Leu Asp Pro Asp Val Ala Gly Arg Pro Glu
         35                  40                  45
Asp Leu Val Val Tyr Gly Gly Ile Gly Lys Ala Ala Arg Asn Trp Ala
     50                  55                  60
Cys Phe Glu Gln Ile Leu Arg Ser Leu Gln Ala Leu Gln Pro Glu Glu
 65                  70                  75                  80
Thr Leu Leu Val Gln Ser Gly Lys Pro Val Gly Val Phe Arg Thr His
                 85                  90                  95
Ala Asp Ala Pro Arg Val Leu Ile Ala Asn Ser Asn Leu Val Pro His
            100                 105                 110
Trp Ala Thr Trp Asp His Phe His Glu Leu Asp Lys Ala Gly Leu Met
        115                 120                 125
Met Tyr Gly Gln Met Thr Ala Gly Ser Trp Ile Tyr Ile Gly Ala Gln
    130                 135                 140
Gly Ile Val Gln Gly Thr Phe Glu Thr Phe Val Glu Ala Gly Arg Lys
145                 150                 155                 160
His Tyr Asn Gly Asp Leu Thr Gly Lys Trp Ile Leu Thr Ala Gly Leu
                165                 170                 175
Gly Gly Met Gly Gly Ala Gln Pro Leu Ala Gly Val Leu Ala Gly Ala
            180                 185                 190
Cys Val Leu Ala Val Glu Cys Gln Glu Ser Arg Ile Asp Phe Arg Leu
        195                 200                 205
Arg Thr Arg Tyr Leu Asp His Lys Ala Phe Ser Val Asp Glu Ala Leu
    210                 215                 220
Ala Ile Ile Asp Lys Ala Cys Lys Glu Lys Arg Ala Ile Ser Val Gly
225                 230                 235                 240
Leu Leu Gly Asn Ala Ala Glu Ile Leu Pro Glu Leu Val Gln Arg Ala
                245                 250                 255
Lys Ala Gly Gly Met Lys Pro Asp Ile Val Thr Asp Gln Thr Ser Ala
            260                 265                 270
His Asp Pro Ile Asn Gly Tyr Leu Pro Ala Gly Trp Asp Leu Ala Arg
        275                 280                 285
Trp Glu Ser Ser Arg Gln Ser Asp Pro Lys Ala Val Glu Lys Ala Ala
    290                 295                 300
Arg Ala Ser Met Ala Val His Val Gln Ala Met Leu Asp Phe Cys His
```

```
                     305                 310                 315                 320
Met Gly Ile Pro Thr Val Asp Tyr Gly Asn Asn Ile Arg Gln Val Ala
                325                 330                 335

Leu Asp Glu Gly Val Lys Asn Ala Phe Asp Phe Pro Gly Phe Val Pro
            340                 345                 350

Ala Tyr Ile Arg Pro Leu Phe Cys Glu Gly Lys Gly Pro Phe Arg Trp
        355                 360                 365

Val Ala Leu Ser Gly Asp Pro Glu Asp Ile Tyr Lys Thr Asp Ala Lys
    370                 375                 380

Leu Lys Ala Leu Phe Pro Glu His Thr Asn Leu His Arg Trp Leu Asp
385                 390                 395                 400

Met Ala Gln Glu Arg Ile Ala Phe Gln Gly Leu Pro Ala Arg Ile Cys
                405                 410                 415

Trp Leu Gly Leu Gly Glu Arg His Leu Ala Gly Leu Ala Phe Asn Glu
            420                 425                 430

Met Val Arg Asn Gly Glu Leu Lys Ala Pro Val Val Ile Gly Arg Asp
        435                 440                 445

His Leu Asp Cys Gly Ser Val Ala Ser Pro Asn Arg Glu Thr Glu Ala
    450                 455                 460

Met Met Asp Gly Ser Asp Ala Val Ser Asp Trp Pro Leu Leu Asn Ala
465                 470                 475                 480

Leu Leu Asn Thr Ala Gly Ala Thr Trp Val Ser Leu His His Gly
                485                 490                 495

Gly Gly Val Gly Met Gly Phe Ser Gln His Ala Gly Val Val Ile Val
            500                 505                 510

Ala Asp Gly Thr Ala Glu Ala Asp Ala Arg Leu Ser Arg Val Leu Trp
        515                 520                 525

Asn Asp Pro Ala Thr Gly Val Met Arg His Ala Asp Ala Gly Tyr Glu
    530                 535                 540

Val Ala Arg Asp Cys Ala Arg Arg His Glu Leu Thr Leu Pro Met Ala
545                 550                 555                 560

Lys Glu Leu Pro

<210> SEQ ID NO 12
<211> LENGTH: 565
<212> TYPE: PRT
<213> ORGANISM: Vibrio cholerae

<400> SEQUENCE: 12

Met Thr Gln Ser Ser Ala Gln Gly Thr Arg Leu Asp Thr Gln Arg Thr
 1               5                  10                  15

Ile Arg Ala Pro Arg Gly Thr Gln Leu Arg Ala Lys Ser Trp Leu Thr
            20                  25                  30

Glu Ala Pro Leu Arg Met Leu Met Asn Asn Leu Asp Pro Asp Val Ala
        35                  40                  45

Glu His Pro His Ala Leu Val Val Tyr Gly Gly Ile Gly Arg Ala Ala
    50                  55                  60

Arg Asn Trp Glu Cys Phe Asp Lys Ile Val Glu Val Leu Glu Arg Leu
65                  70                  75                  80

Glu Asp Asp Gln Thr Leu Leu Val Gln Ser Gly Lys Pro Val Gly Val
                85                  90                  95

Phe Pro Thr His Lys Asn Ala Pro Arg Val Leu Ile Ala Asn Ser Asn
            100                 105                 110

Leu Val Pro His Trp Ala Asn Trp Glu His Phe Asn Glu Leu Asp Lys
```

-continued

```
            115                 120                 125
Gln Gly Leu Met Met Tyr Gly Gln Met Thr Ala Gly Ser Trp Ile Tyr
    130                 135                 140
Ile Gly Ser Gln Gly Ile Val Gln Gly Thr Tyr Glu Thr Phe Val Ala
145                 150                 155                 160
Val Ala Lys Lys His Phe Asn Gly Asp Ala Lys Gly Arg Trp Val Leu
                165                 170                 175
Thr Gly Gly Leu Gly Gly Met Gly Gly Ala Gln Pro Leu Ala Ala Thr
                180                 185                 190
Met Ala Gly Phe Ser Met Ile Ala Val Glu Cys Asp Glu Ser Arg Ile
                195                 200                 205
Asp Tyr Arg Leu Arg Thr Gly Tyr Val Asp Lys Ala Asn Thr Leu
    210                 215                 220
Asp Glu Ala Leu Ala Met Ile Ala Asp Thr Asp Arg Pro Ile Ser Val
225                 230                 235                 240
Gly Leu Leu Gly Asn Ala Ala Asp Ile Phe Pro Glu Leu Val Lys Arg
                245                 250                 255
Asn Ile Thr Pro Asp Val Val Thr Asp Gln Thr Ser Ala His Asp Pro
                260                 265                 270
Leu Asn Gly Tyr Leu Pro Leu Gly Trp Ser Met Glu Lys Ala Ala Gln
                275                 280                 285
Met Arg Gln Gln Asn Glu Ala Glu Val Val Lys Ala Ala Lys Ala Ser
                290                 295                 300
Met Ala Ile Gln Val Arg Ala Met Leu Asp Leu Gln Thr Arg Gly Ala
305                 310                 315                 320
Ala Thr Leu Asp Tyr Gly Asn Asn Ile Arg Gln Met Ala Leu Glu Glu
                325                 330                 335
Gly Val Ala Asn Ala Phe Asp Phe Pro Gly Phe Val Pro Ala Tyr Ile
                340                 345                 350
Arg Pro Leu Phe Cys Glu Gly Ile Gly Pro Phe Arg Trp Ala Ala Leu
                355                 360                 365
Ser Gly Asp Pro Glu Asp Ile Tyr Lys Thr Asp Gln Lys Val Lys Glu
    370                 375                 380
Leu Ile Pro Asp Asn Pro His Leu His Asn Trp Leu Asp Met Ala Arg
385                 390                 395                 400
Glu Arg Ile His Phe Gln Gly Leu Pro Ala Arg Ile Cys Trp Val Gly
                405                 410                 415
Leu Lys Asp Arg Ala Arg Leu Gly Leu Ala Phe Asn Glu Met Val Lys
                420                 425                 430
Asn Gly Glu Leu Lys Ala Pro Ile Val Ile Gly Arg Asp His Leu Asp
                435                 440                 445
Ser Gly Ser Val Ala Ser Pro Asn Arg Glu Thr Glu Gly Met Leu Asp
    450                 455                 460
Gly Ser Asp Ala Val Ser Asp Trp Pro Leu Leu Asn Ala Leu Leu Asn
465                 470                 475                 480
Thr Ala Gly Gly Ala Thr Trp Val Ser Leu His His Gly Gly Val
                485                 490                 495
Gly Met Gly Phe Ser Gln His Ser Gly Met Val Ile Cys Cys Asp Gly
                500                 505                 510
Ser Asp Asp Ala Ala Glu Arg Ile Ala Arg Val Leu His Asn Asp Pro
    515                 520                 525
Ala Thr Gly Val Met Arg His Ala Asp Ala Gly Tyr Glu Ile Ala Lys
    530                 535                 540
```

Arg Cys Ala Gln Gln Lys Leu Asp Leu Pro Met Leu Asn Ala Glu
545                 550                 555                 560

Leu Ala Lys Leu Lys
            565

<210> SEQ ID NO 13
<211> LENGTH: 565
<212> TYPE: PRT
<213> ORGANISM: Pseudomonas syringae

<400> SEQUENCE: 13

Met Thr Ser Thr Thr Pro Lys Ser Pro Ala Ala Phe Thr Arg His Arg
 1               5                  10                  15

Asp Gly Glu Ile Arg Ala Ala Arg Gly Thr Gln Leu Thr Ala Lys Ser
            20                  25                  30

Trp Met Thr Glu Ala Pro Leu Arg Met Leu Met Asn Asn Leu Asp Pro
        35                  40                  45

Gln Val Ala Glu Asn Pro Thr Glu Leu Val Val Tyr Gly Gly Ile Gly
    50                  55                  60

Arg Ala Ala Arg Asn Trp Glu Cys Tyr Asp Lys Ile Val Glu Ser Leu
65                  70                  75                  80

Thr Asn Leu Asn Asp Asp Glu Thr Leu Leu Val Gln Ser Gly Lys Pro
                85                  90                  95

Val Gly Val Phe Lys Thr His Ser Asn Ala Pro Arg Val Leu Ile Ala
            100                 105                 110

Asn Ser Asn Leu Val Pro His Trp Ala Thr Trp Glu His Phe Asn Glu
        115                 120                 125

Leu Asp Ala Lys Gly Leu Ala Met Tyr Gly Gln Met Thr Ala Gly Ser
    130                 135                 140

Trp Ile Asn Ile Gly Ser Gln Gly Ile Val Gln Gly Thr Tyr Glu Thr
145                 150                 155                 160

Phe Val Glu Ala Gly Arg Gln His Tyr Asn Gly Ser Leu Lys Gly Lys
                165                 170                 175

Trp Val Leu Thr Ala Gly Leu Gly Gly Met Gly Gly Ala Gln Pro Leu
            180                 185                 190

Ala Ala Thr Leu Ala Gly Ala Cys Ser Leu Asn Ile Glu Cys Gln Gln
        195                 200                 205

Ser Arg Ile Asp Phe Arg Leu Ala Thr Arg Tyr Val Asp Glu Gln Ala
    210                 215                 220

Leu Asp Leu Asp Asp Ala Leu Val Arg Ile Ala Lys Tyr Thr Ala Glu
225                 230                 235                 240

Gly Lys Ala Ile Ser Ile Ala Leu Cys Gly Asn Ala Ala Glu Leu Leu
                245                 250                 255

Pro Glu Met Val Arg Arg Gly Val Arg Pro Asp Met Val Thr Asp Gln
            260                 265                 270

Thr Ser Ala His Asp Pro Leu Asn Gly Tyr Leu Pro Lys Gly Trp Thr
        275                 280                 285

Trp Glu Gln Tyr Arg Asp Arg Ala Val Thr Asp Pro Ala Ala Val Val
    290                 295                 300

Lys Ala Ala Lys Ala Ser Met Gly Glu His Val Glu Ala Met Leu Ala
305                 310                 315                 320

Phe Gln Lys Ala Gly Ile Pro Thr Phe Asp Tyr Gly Asn Asn Ile Arg
                325                 330                 335

Gln Met Ala Lys Glu Val Gly Val Glu Asn Ala Phe Asp Phe Pro Gly

```
                  340                 345                 350
Phe Val Pro Ala Tyr Ile Arg Pro Leu Phe Cys Arg Gly Val Gly Pro
            355                 360                 365
Phe Arg Trp Val Ala Leu Ser Gly Asp Ala Glu Asp Ile Tyr Lys Thr
        370                 375                 380
Asp Ala Lys Val Lys Glu Leu Ile Ala Asp Ala His Leu His Asn
385                 390                 395                 400
Trp Leu Asp Met Ala Arg Glu Arg Ile Ser Phe Gln Gly Leu Pro Ala
                405                 410                 415
Arg Ile Cys Trp Val Gly Leu Gly Gln Arg Ala Lys Leu Gly Leu Ala
            420                 425                 430
Phe Asn Glu Met Val Arg Ser Gly Glu Leu Lys Ala Pro Ile Val Ile
            435                 440                 445
Gly Arg Asp His Leu Asp Ser Gly Ser Val Ser Pro Asn Arg Glu
        450                 455                 460
Thr Glu Ser Met Lys Asp Gly Ser Asp Ala Val Ser Asp Trp Pro Leu
465                 470                 475                 480
Leu Asn Ala Leu Leu Asn Thr Ala Ser Gly Ala Thr Trp Val Ser Leu
                485                 490                 495
His His Gly Gly Gly Val Gly Met Gly Phe Ser Gln His Ser Gly Met
                500                 505                 510
Val Ile Val Cys Asp Gly Thr Asp Glu Ala Ala Glu Arg Ile Ala Arg
            515                 520                 525
Val Leu His Asn Asp Pro Ala Thr Gly Val Met Arg His Ala Asp Ala
        530                 535                 540
Gly Tyr Asp Ile Ala Ile Asp Cys Ala Asn Glu Gln Gly Leu Asn Leu
545                 550                 555                 560
Pro Met Ile Asn Gly
                565

<210> SEQ ID NO 14
<211> LENGTH: 552
<212> TYPE: PRT
<213> ORGANISM: Bacillus subtilis

<400> SEQUENCE: 14

Met Thr Asp Val Lys Lys Ser Ile Arg Ala Asn Arg Gly Thr Glu Leu
  1               5                  10                  15
Glu Cys Leu Gly Trp Glu Gln Glu Ala Val Leu Arg Met Leu Arg Asn
                 20                  25                  30
Asn Leu Asp Pro Glu Val Ala Glu Lys Pro Glu Asp Leu Ile Val Tyr
             35                  40                  45
Gly Gly Ile Gly Lys Ala Ala Arg Asp Trp Asp Ala Phe His Ala Ile
         50                  55                  60
Glu His Ser Leu Lys Thr Leu Lys Asn Asp Glu Thr Leu Leu Val Gln
 65                  70                  75                  80
Ser Gly Lys Pro Val Gly Met Phe Arg Thr His Pro Gln Ala Pro Arg
                 85                  90                  95
Val Leu Leu Ala Asn Ser Val Leu Val Pro Lys Trp Ala Asp Trp Glu
            100                 105                 110
His Phe His Glu Leu Glu Lys Lys Gly Leu Met Met Tyr Gly Gln Met
        115                 120                 125
Thr Ala Gly Ser Trp Ile Tyr Ile Gly Ser Gln Gly Ile Leu Gln Gly
    130                 135                 140
```

-continued

```
Thr Tyr Glu Thr Phe Ala Glu Leu Ala Arg Gln His Phe Gly Gly Ser
145                 150                 155                 160

Leu Lys Gly Thr Leu Thr Leu Thr Ala Gly Leu Gly Gly Met Gly Gly
            165                 170                 175

Ala Gln Pro Leu Ser Val Thr Met Asn Glu Gly Val Val Ile Ala Val
            180                 185                 190

Glu Val Asp Glu Lys Arg Ile Asp Lys Arg Ile Glu Thr Lys Tyr Cys
            195                 200                 205

Asp Arg Lys Thr Ala Ser Ile Glu Glu Ala Leu Ala Trp Ala Glu Glu
            210                 215                 220

Ala Lys Leu Ala Gly Lys Pro Leu Ser Ile Ala Leu Leu Gly Asn Ala
225                 230                 235                 240

Ala Glu Val His His Thr Leu Leu Asn Arg Gly Val Lys Ile Asp Ile
            245                 250                 255

Val Thr Asp Gln Thr Ser Ala His Asp Pro Leu Ile Gly Tyr Val Pro
            260                 265                 270

Glu Gly Tyr Ser Leu Asp Glu Ala Asp Arg Leu Arg Gln Asp Thr Pro
            275                 280                 285

Glu Leu Tyr Val Arg Leu Ala Lys Gln Ser Met Lys Lys His Val Glu
            290                 295                 300

Ala Met Leu Ala Phe Gln Gln Lys Gly Ser Ile Val Phe Asp Tyr Gly
305                 310                 315                 320

Asn Asn Ile Arg Gln Val Ala Lys Asp Glu Gly Leu Glu Asn Ala Phe
            325                 330                 335

Asp Phe Pro Gly Phe Val Pro Ala Tyr Ile Arg Pro Leu Phe Cys Glu
            340                 345                 350

Gly Lys Gly Pro Phe Arg Trp Ala Ala Leu Ser Gly Asp Pro Ala Asp
            355                 360                 365

Ile Tyr Arg Thr Asp Ala Leu Leu Lys Glu Leu Phe Pro Thr Asn Lys
            370                 375                 380

Ala Leu His Arg Trp Ile Asp Met Ala Gln Glu Lys Val Thr Phe Gln
385                 390                 395                 400

Gly Leu Pro Ser Arg Ile Cys Trp Leu Gly Tyr Gly Glu Arg Lys Lys
            405                 410                 415

Met Gly Leu Ala Ile Asn Glu Leu Val Arg Thr Gly Glu Leu Lys Ala
            420                 425                 430

Pro Val Val Ile Gly Arg Asp His Leu Asp Cys Gly Ser Val Ala Ser
            435                 440                 445

Pro Asn Arg Glu Thr Glu Ala Met Lys Asp Gly Ser Asp Ala Val Gly
            450                 455                 460

Asp Trp Ala Val Leu Asn Ala Leu Val Asn Thr Ala Gly Ala Gly Ser
465                 470                 475                 480

Trp Val Ser Phe His His Gly Gly Val Gly Met Gly Tyr Ser Leu
            485                 490                 495

His Ala Gly Met Val Ala Val Ala Asp Gly Ser Glu Leu Ala Asp Glu
            500                 505                 510

Arg Leu Ala Arg Val Leu Thr Ser Asp Pro Gly Met Gly Ile Ile Arg
            515                 520                 525

His Ala Asp Ala Gly Tyr Glu Arg Ala Val Glu Val Ala Lys Glu Gln
            530                 535                 540

Asp Ile Ile Val Pro Met Gln Lys
545                 550
```

<210> SEQ ID NO 15
<211> LENGTH: 572
<212> TYPE: PRT
<213> ORGANISM: Streptomyces coelicolor

<400> SEQUENCE: 15

Met Ser Gly Pro Arg Pro Val Arg Ala Pro Arg Gly Thr Glu Pro Ser
1               5                   10                  15

Ala Leu Gly Trp Gln Gln Glu Ala Ala Leu Arg Met Leu Gln Asn Asn
            20                  25                  30

Leu Asp Pro Glu Val Ala Glu His Pro Asp Lys Leu Val Val Tyr Gly
        35                  40                  45

Gly Thr Gly Lys Ala Ala Arg Asp Trp Arg Ser Phe Asp Ala Met Val
    50                  55                  60

Arg Thr Leu Arg Thr Leu Lys Gln Asp Glu Thr Met Leu Val Gln Ser
65                  70                  75                  80

Gly Arg Pro Val Gly Val Met Gln Thr His Glu Trp Ala Pro Arg Val
                85                  90                  95

Leu Ile Ala Asn Ser Asn Leu Val Gly Asp Trp Ala Asn Trp Glu Glu
            100                 105                 110

Phe Arg Arg Leu Glu Ala Leu Gly Leu Thr Met Tyr Gly Gln Met Thr
        115                 120                 125

Ala Gly Ser Trp Ile Tyr Ile Gly Thr Gln Gly Ile Leu Gln Gly Thr
    130                 135                 140

Tyr Glu Thr Phe Ala Ala Val Ala Ala Lys Lys Phe Gly Gly Thr Leu
145                 150                 155                 160

Ala Gly Thr Ile Thr Leu Thr Ala Gly Leu Gly Gly Met Gly Gly Ala
                165                 170                 175

Gln Pro Leu Ala Val Thr Met Asn Asp Gly Val Val Ile Cys Val Asp
            180                 185                 190

Cys Asp Pro Arg Ala Ile Asp Arg Arg Ile Glu His His Tyr Leu Asp
        195                 200                 205

Val Lys Ala Asp Ser Leu Asp His Ala Leu Gln Leu Ala Thr Glu Ala
    210                 215                 220

Arg Asp Arg Arg Lys Pro Leu Ser Ile Gly Val Leu Gly Asn Ala Ala
225                 230                 235                 240

Glu Leu Val Pro Gln Leu Leu Ala Met Gly Ala Pro Ile Asp Ile Val
                245                 250                 255

Thr Asp Gln Thr Ser Ala His Asp Pro Leu Ala Tyr Leu Pro Thr Gly
            260                 265                 270

Ile Ala Phe Glu Asp Met Ala Asp Ala Ala Lys Asp Pro Ala Gly
        275                 280                 285

Phe Thr Thr Arg Ala Arg Glu Ser Met Ala Arg His Val Glu Ala Met
    290                 295                 300

Val Gly Phe Gln Asp Ala Gly Ala Glu Val Phe Asp Tyr Gly Asn Ser
305                 310                 315                 320

Ile Arg Gly Glu Ala Gln Leu Ala Gly Tyr Asp Arg Ala Phe Ala Phe
                325                 330                 335

Pro Gly Phe Val Pro Ala Tyr Ile Arg Pro Leu Phe Cys Glu Gly Lys
            340                 345                 350

Gly Pro Phe Arg Trp Ala Ala Leu Ser Gly Asp Pro Ala Asp Ile Ala
        355                 360                 365

Lys Thr Asp Lys Ala Ile Leu Asp Leu Phe Pro Glu Asn Glu Ser Leu
    370                 375                 380

```
Ala Arg Trp Ile Lys Met Ala Gly Glu Arg Val His Phe Gln Gly Leu
385                 390                 395                 400

Pro Ala Arg Ile Cys Trp Leu Gly Tyr Gly Glu Arg Asp Lys Ala Gly
            405                 410                 415

Glu Arg Phe Asn Asp Met Val Ala Ser Gly Leu Ala Ala Pro Ile
                420                 425                 430

Val Ile Gly Arg Asp His Leu Asp Cys Gly Ser Val Ala Ser Pro Tyr
            435                 440                 445

Arg Glu Thr Glu Ala Met Leu Asp Gly Ser Asp Ala Ile Ala Asp Trp
        450                 455                 460

Pro Leu Leu Asn Ala Met Val Asn Val Ala Ser Gly Ala Ser Trp Val
465                 470                 475                 480

Ser Leu His His Gly Gly Val Gly Met Gly Arg Ser Ile His Ala
                485                 490                 495

Gly Gln Val Thr Val Ala Asp Gly Thr Pro Leu Ala Gly Glu Lys Ile
                500                 505                 510

Arg Arg Val Leu Thr Asn Asp Pro Gly Met Gly Val Ile Arg His Val
            515                 520                 525

Asp Ala Gly Tyr Asp Ile Ala Glu Ser Val Ala Ala Glu Arg Asp Val
        530                 535                 540

Arg Val Pro Met Arg Glu Gly Asp Glu Ala His Glu Gly Asp Ala Ala
545                 550                 555                 560

His Gly Ser Gly Ala Ala Arg Glu Gly Asp Gly Val
                565                 570

<210> SEQ ID NO 16
<211> LENGTH: 558
<212> TYPE: PRT
<213> ORGANISM: Deinococcus radiodurans

<400> SEQUENCE: 16

Met Thr Thr His Glu Pro Arg Thr Val Arg Ala Pro Arg Gly Pro His
1               5                   10                  15

Lys Thr Ala Lys Gly Trp Ile Gln Glu Ala Ala Lys Arg Met Leu Met
            20                  25                  30

Asn Asn Leu Asp Pro Glu Val Ala Glu His Pro Glu Ser Leu Val Val
        35                  40                  45

Tyr Gly Gly Arg Gly Lys Ala Ala Arg Asn Trp Glu Ala Phe Asp His
    50                  55                  60

Ile Val Ala Thr Leu Asp Arg Leu Glu Asn Asp Glu Thr Leu Leu Val
65                  70                  75                  80

Gln Ser Gly Lys Pro Val Ala Val Leu Arg Thr His Glu Trp Ala Pro
                85                  90                  95

Arg Val Leu Ile Ala Asn Ser Asn Leu Val Pro His Trp Ala Asn Trp
            100                 105                 110

Glu Thr Phe Asp Lys Leu Asp Gln Ala Gly Leu Met Met Tyr Gly Gln
        115                 120                 125

Met Thr Ala Gly Ser Trp Ile Tyr Ile Gly Thr Gln Gly Ile Leu Gln
    130                 135                 140

Gly Thr Tyr Glu Thr Phe Ala Gly Ala Ala Gln Lys His Phe Gly Gly
145                 150                 155                 160

Ser Leu Lys Gly Thr Ile Thr Val Thr Ala Gly Leu Gly Gly Met Gly
                165                 170                 175

Gly Ala Gln Pro Leu Ala Val Lys Leu Ala Gly Gly Val Ser Ile Thr
            180                 185                 190
```

```
Ile Glu Ile Asp Pro Thr Arg Ile Arg Lys Arg Leu Glu Thr Arg Tyr
        195                 200                 205

Leu Asp Glu Val Ala Asp Asn Leu Gln Asp Ala Ile Ala Arg Ala Glu
    210                 215                 220

Gly Tyr Lys Ala Gln Gly Val Ala Arg Ser Ile Gly Val Gln Gly Asn
225                 230                 235                 240

Ala Ala Glu Leu Val Pro Gln Leu Val Glu Met Asn Trp Thr Pro Asp
                245                 250                 255

Leu Leu Thr Asp Gln Thr Ser Ala His Asp Pro Met Trp Gly Tyr Ile
            260                 265                 270

Pro Pro Val Asn Ala Asp Glu Asp Ala Gly Lys Leu Arg Ser Glu His
        275                 280                 285

Ala Glu Glu Tyr Arg Gln Arg Ala Tyr Ala Ala Met Ala Ala His Val
    290                 295                 300

Arg Ala Met Leu Glu Leu Gln Lys Arg Gly Ala Val Thr Phe Asp Tyr
305                 310                 315                 320

Gly Asn Asn Leu Arg Gln Arg Ala Phe Glu Ala Gly Val Glu Asp Ala
                325                 330                 335

Phe Ser Tyr Pro Gly Phe Val Pro Ala Phe Ile Arg Asp Ser Phe Cys
            340                 345                 350

Glu Gly Arg Gly Pro Phe Arg Trp Val Ala Leu Ser Gly Asp Pro Gln
        355                 360                 365

Asp Ile Tyr Ala Thr Asp Lys Ala Leu Leu Glu Leu Phe Pro Glu Asp
    370                 375                 380

Glu Arg Leu Gln Ser Trp Leu Thr Tyr Ala Ala Asp Gln Ile Ala Phe
385                 390                 395                 400

Gln Gly Leu Pro Ala Arg Ile Cys Trp Leu Gly Tyr Lys Glu Arg Asp
                405                 410                 415

Arg Ala Ala Lys Leu Phe Asn Asp Met Val Lys Asp Gly Arg Val Lys
            420                 425                 430

Ala Pro Ile Val Ile Gly Arg Asp His Leu Asp Ala Gly Ser Val Ala
        435                 440                 445

Ser Pro Tyr Arg Glu Thr Glu Ala Met Lys Asp Gly Ser Asp Ala Val
    450                 455                 460

Ser Asp Trp Pro Leu Leu Asn Phe Gly Val Gly Ile Ala Ser Gly Ala
465                 470                 475                 480

Ser Trp Met Ser Phe His His Gly Gly Val Gly Leu Gly Phe Ser
                485                 490                 495

Gln His Ser Gly Leu Val Ile Val Ala Asp Gly Thr Asp Glu Ala Ala
            500                 505                 510

Lys Lys Leu Ser Arg Ala Leu Thr Asn Asp Pro Gly Met Gly Val Ile
        515                 520                 525

Arg His Ala Asp Ala Gly Tyr Asp His Ala Leu Asp Val Ala Arg Glu
    530                 535                 540

Arg Gly Ile Asp Leu Pro Ser Leu Gly Ile Lys Asp His Ala
545                 550                 555

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Highly
      conserved active site present in multiple
      organisms
```

```
<400> SEQUENCE: 17

Phe Gln Gly Leu Pro Ala Arg Ile Cys Trp
 1               5                  10

<210> SEQ ID NO 18
<211> LENGTH: 640
<212> TYPE: DNA
<213> ORGANISM: Pseudomonas syringae

<400> SEQUENCE: 18
ctgcagctga acgacaacag tgaactgctg gaaatcacgg taaccggccg ctgctgtgtg      60
attgagttga gcgggatcta agccgcacat acacctctgt aggagcgagc ttgctcgcga     120
gctcttgaat gcggccacca agagctcgct cctgcaaggt ttgagtcatt gctgcgcccc     180
atcttgttac cgaacgcccc aaaaagacgc aaaaccccccg cttcagtaac atccctgcgc    240
tttgcccttt actccctgca aaaatccttt catccctcat cgccttgatt ttcgtgcctt     300
gcagcttcga atacttaaat ttcacgggct gatatcgcac cttggccgct tacttgcata     360
tgcttgtatg tacaagtaca taagtgtgcg tcgaccctct tgtccccgac gcatctgccc     420
atcgctgagg agttacccgt gacttcaact acccctaaat cgccagctgc gtttacccgt     480
catcgtgatg gtgaaatccg cgccgcccgc ggtacccagc tcactgccaa agctggatg     540 accgaagctc cgctgcggat gttgatgaac aacctcgacc cgcaagtggc cgagaacccg     600
accgaactgg tggtatatgg cggtattggg cgtgcagcgc                           640

<210> SEQ ID NO 19
<211> LENGTH: 14
<212> TYPE: DNA
<213> ORGANISM: Pseudomonas syringae

<400> SEQUENCE: 19
cttgtatgta caag                                                       14

<210> SEQ ID NO 20
<211> LENGTH: 22
<212> TYPE: DNA
<213> ORGANISM: Pseudomonas syringae

<400> SEQUENCE: 20
aagtgtgcgt cgaccctctt gt                                              22

<210> SEQ ID NO 21
<211> LENGTH: 5
<212> TYPE: PRT
<213> ORGANISM: Pseudomonas syringae

<400> SEQUENCE: 21

Ser Leu Asn Ile Glu
 1               5

<210> SEQ ID NO 22
<211> LENGTH: 17
<212> TYPE: DNA
<213> ORGANISM: Pseudomonas syringae
<220> FEATURE:
<221> NAME/KEY: modified_base
<222> LOCATION: (9)
<223> OTHER INFORMATION: variable nucleotide

<400> SEQUENCE: 22
```

```
aagtgtgcnc ctcttgt                                              17

<210> SEQ ID NO 23
<211> LENGTH: 14
<212> TYPE: DNA
<213> ORGANISM: Artificial Sequence
<220> FEATURE:
<223> OTHER INFORMATION: Description of Artificial Sequence:
      Illustrative promoter element in Pseudomonas syringae
<220> FEATURE:
<221> NAME/KEY: modified_base
<222> LOCATION: (3)..(12)
<223> OTHER INFORMATION: variable nucleotide

<400> SEQUENCE: 23
ggnnnnnnnn nngc                                                 14

<210> SEQ ID NO 24
<211> LENGTH: 12
<212> TYPE: DNA
<213> ORGANISM: Artificial Sequence
<220> FEATURE:
<223> OTHER INFORMATION: Description of Artificial Sequence:
      Illustrative promoter element in Pseudomonas syringae
<220> FEATURE:
<221> NAME/KEY: modified_base
<222> LOCATION: (4)..(9)
<223> OTHER INFORMATION: variable nucleotide

<400> SEQUENCE: 24
atannnnnnt at                                                   12

<210> SEQ ID NO 25
<211> LENGTH: 40
<212> TYPE: DNA
<213> ORGANISM: Pseudomonas syringae

<400> SEQUENCE: 25
ttgctcgcga gctcttgaat gcggccaaca agagctcgct                     40

<210> SEQ ID NO 26
<211> LENGTH: 14
<212> TYPE: DNA
<213> ORGANISM: Artificial Sequence
<220> FEATURE:
<223> OTHER INFORMATION: Description of Artificial Sequence:
      Illustrative promoter element in Pseudomonas syringae
<220> FEATURE:
<221> NAME/KEY: modified_base
<222> LOCATION: (3)..(12)
<223> OTHER INFORMATION: variable nucleotide

<400> SEQUENCE: 26
ggnnnnnnnn nngg                                                 14
```